(12) United States Patent
Askenasy

(10) Patent No.: US 8,435,786 B2
(45) Date of Patent: May 7, 2013

(54) METHODS OF SELECTING STEM CELLS AND USES THEREOF

(75) Inventor: Nadir Askenasy, Tel Aviv (IL)

(73) Assignee: Cellect Biotechnology Ltd., Kfar-Saba (IL)

( * ) Notice: Subject to any disclaimer, the term of this patent is extended or adjusted under 35 U.S.C. 154(b) by 829 days.

(21) Appl. No.: 12/227,865

(22) PCT Filed: May 31, 2007

(86) PCT No.: PCT/IL2007/000663
§ 371 (c)(1), (2), (4) Date: Oct. 14, 2009

(87) PCT Pub. No.: WO2007/138597
PCT Pub. Date: Dec. 6, 2007

(65) Prior Publication Data
US 2010/0040582 A1 Feb. 18, 2010

Related U.S. Application Data

(60) Provisional application No. 60/809,390, filed on May 31, 2006, provisional application No. 60/840,013, filed on Aug. 25, 2006.

(51) Int. Cl.
*C12N 5/00* (2006.01)

(52) U.S. Cl.
USPC ........... 435/375; 435/377; 435/325; 424/93.7

(58) Field of Classification Search .................. None
See application file for complete search history.

(56) References Cited

U.S. PATENT DOCUMENTS

| | | | |
|---|---|---|---|
| 4,642,120 A | 2/1987 | Nevo | |
| 5,464,764 A | 11/1995 | Capecchi | |
| 5,486,359 A | 1/1996 | Caplan | |
| 5,487,992 A | 1/1996 | Capecchi | |
| 5,654,186 A | 8/1997 | Cerami | |
| 5,716,411 A | 2/1998 | Orgill | |
| 5,716,616 A | 2/1998 | Prockop | |
| 5,736,396 A | 4/1998 | Bruder | |
| 6,146,888 A * | 11/2000 | Smith et al. | 435/325 |
| 6,184,035 B1 * | 2/2001 | Csete et al. | 435/377 |
| 6,531,505 B2 * | 3/2003 | Xu et al. | 514/456 |
| 6,747,013 B2 * | 6/2004 | Firestein et al. | 514/44 R |
| 6,951,919 B1 | 10/2005 | Nagata | |
| 2004/0018170 A1 | 1/2004 | Shirwan | |
| 2004/0131599 A1 | 7/2004 | Civin et al. | |
| 2005/0124003 A1 | 6/2005 | Atala | |
| 2005/0181504 A1 | 8/2005 | Merchav | |
| 2005/0265980 A1 | 12/2005 | Chen | |
| 2005/0276793 A1 | 12/2005 | Milhem | |
| 2006/0018885 A1 | 1/2006 | Ildstad | |

FOREIGN PATENT DOCUMENTS

| | | |
|---|---|---|
| WO | WO 2004/003142 | 1/2004 |
| WO | 2005/109199 A2 | 11/2005 |
| WO | WO 2005/109199 | 11/2005 |
| WO | WO 2007/138597 | 12/2007 |

OTHER PUBLICATIONS

Gordon EM et al. 1997. Capture and expansion of bone marrow-derived mesenchymal progenitor cells with a transforming growth factor-beta1-von Willebrand's factor fusion protein for retrovirus-mediated delivery of coagulation factor IX. Hum Gene Ther 8: 1385-1394.*
Pearl-Yafe M et al. 2007. Expression of Fas and Fas-ligand in donor hematopoietic stem and progenitor cells is dissociated from the sensitivity to apoptosis. Exp Hematol 35: 1601-1612.*
Communication Pursuant to Article 94(3) EPC Dated Jul. 23, 2010 From the European Patent Office Re. Application No. 07736403.2.
Response Dated Jan. 25, 2011 to Communication Pursuant to Article 94(3) EPC of Jul. 23, 2010 From the European Patent Office Re. Application No. 07736403.2.
International Preliminary Report on Patentability Dated Dec. 18, 2008 From the International Bureau of WIPO Re.: Application No. PCT/IL2007/000663.
International Search Report and the Written Opinion Dated Feb. 27, 2008 From the International Searching Authority Re. Application No. PCT/IL2007/000663.
Josefsen et al. "Fas Ligand Promotes Cell Survival of Immature Human Bone Marrow CD34+CD38− Hematopoietic Progenitor Cells by Suppressing Apoptosis", Experimental Hematology, XP000984554, 27(9): 1451-1459, Sep. 1999.
Pearl-Yafe et al. "Fas Ligand Enhances Hematopoietic Cell Engraftment Through Abrogation of Alloimmune Responses and Nonimmunogenic Interactions", Stem Cells, XP009096055, 25(6): 1448-1455, Jun. 2007.
Aggarwal BB., (2003) Signalling pathways of the TNF superfamily: a double-edged sword. Nat Rev Immunol. 3:745-56.
Ashkenazi A., (2002) Targeting death and decoy receptors of the tumour-necrosis factor superfamily. Nat Cancer Rev. 2:420-30.
Askenasy N. et al., (2003) Display of Fas ligand protein on cardiac vasculature as a novel means of regulating allograft rejection. Circulation 107:1525-31.
Askenasy et al., (2005) Induction of tolerance using Fas ligand: a double-edged immunomodulator. Blood. 105:1396-404.
Askenazy N. et al., (2006) Our perception of developmental plasticity: esse est percipi (to be is to be perceived)? Current Stem Cell Research and Therapy 1:85-94.
Barcena A. et al., (1999) Role of CD95/Fas and its ligand in the regulation of the growth of human CD34++ CD38− fetal liver cells. Exp Hematol. 27:1428-39.

(Continued)

*Primary Examiner* — Lora E Barnhart Driscoll
(74) *Attorney, Agent, or Firm* — Browdy and Neimark, PLLC

(57) ABSTRACT

A method of selecting stem cells from heterogeneous population of cells is disclosed. The method comprises contacting the population of cells with an apoptosis inducing agent under conditions which are apoptotic to non-stem cells and non-apoptotic to stem cells, thereby selecting the stem cells from the heterogeneous population of cells. The selected stem cells may then be used for a variety of applications including transportation and differentiation.

48 Claims, 16 Drawing Sheets

OTHER PUBLICATIONS

Berenson et al., (1988) Antigen CD34+ marrow cells engraft lethally irradiated baboons. J Clin Invest 81:951-5.

Bhardwaj A. and Aggarwal BB., (2003) Receptor-mediated choreography of life and death. J Clin Immunol.23:317-32.

Bohana-Kashtan O. and Civin CI., (2004) Fas ligand as a tool for immunosuppression and generation of immune tolerance. Stem Cells. 22:908-24.

Bohmer RM. et al., (2002) Fetal cell isolation from maternal blood cultures by flow cytometric hemoglobin profiles. Results of a preliminary clinical trial. Fetal Diagn Ther 17:83-9.

Brazelton TR. et al., (2000) From marrow to brain: expression of neuronal phenotypes in adult mice. Science 290:1775-9.

Bryder D. et al., (2001) Self-renewal of multipotent long-term repopulating hematopoietic stem cells is negatively regulated by Fas and tumor necrosis factor receptor activation. J Exp Med 194: 941-52.

Chen et al., (2003) High-dose chemotherapy and hematopoietic stem cell transplantation for patients with nasopharyngeal cancer: a feasibility study. Jpn J Clin Oncol 33:331-5.

Civin et al., (1984) Antigenic analysis of hematopoiesis. III. A hematopoietic progenitor cell surface antigen defined by a monoclonal antibody raised against KG-1a cells. J Immunol 133:157-65.

Cohen JJ. and Duke RC., (1992) Apoptosis and programmed cell death in immunity.Ann Rev Immunol. 10:267-93.

Curtin JF. and Cotter TG., (2003) Live and let die: regulatory mechanisms in Fas-mediated apoptosis. Cell Signal. 15:983-92.

Dao et al., (2000) CD34: to select or not to select? That is the question.Leukemia 14:773-776.

Dempsey PW. et al., (2003) The signalling adaptors and pathways activated by TNF superfamily. Cytokine Growth Factor Rev. 14:193-209.

Di Pietro R. and Zauli G., (2004) Emerging non-apoptotic functions of tumor necrosis factor-related apoptosis-inducing ligand (TRAIL)/Apo2L. J Cell Physiol. 201:331-40.

Dybedal I. et al., (2003) Human reconstituting hematopoietic stem cells up-regulate Fas expression upon active cell cycling but remain resistant to Fas-induced suppression. Blood. 102:118-26.

Gaur U. and Aggarwal BB., (2003) Regulation of proliferation, survival and apoptosis by members of the TNF superfamily. Biochem Pharmacol. 66:1403-8.

Gratwohl et al., (2004) Hematopoetic stem cell transplantation for solid tumors in Europe. Ann Oncol 15:653-60.

Gur H. et al., (2005) Immune regulatory activity of CD34+ progenitor cells: evidence for a deletion-based mechanism mediated by TNF-alpha. Blood. 105:2585-93.

Iwasaki T. et al., (1999) Effect of graft-versus-host disease (GVHD) on host hematopoietic progenitor cells is mediated by Fas-Fas ligand interactions but this does not explain the effect of GVHD on donor cells. Cell Immunol. 197:30-8.

Jang YY. et al., (2004) Hematopoietic stem cells convert into liver cells within days without fusion. Nat Cell Biol. 6:532-9.

Kim H. et al., (2002) Human CD34+ hematopoietic stem/progenitor cells express high levels of FLIP and are resistant to Fas-mediated apoptosis. Stem Cells. 20:174-82.

Kobari L. et al., (2001) CD133+ cell selection is an alternative to CD34+ cell selection for ex vivo expansion of hematopoietic stem cells. J Hematother Stem Cell Res. 10:273-81.

Krause DS. et al., (2001) Multi-organ, multi-lineage engraftment by a single bone marrow-derived stem cell. Cell 105:369-77.

Leff al., (1986) Phase II trial of high-dose melphalan and autologous bone marrow transplantation for metastatic colon carcinoma. J Clin Oncol 4:1586-91.

Liu B. et al., (2003) Homing defect of cultured human hematopoietic cells in the NOD/SCID mouse is mediated by Fas/CD95. Exp Hematol.31:824-32.

Maciejewski J. et al., (1995) Fas antigen expression on CD34+ human marrow cells is induced by interferon gamma and tumor necrosis factor alpha and potentiates cytokine-mediated hematopoietic suppression in vitro. Blood. 85:3183-90.

Miraglia S. et al., (1997) A novel five-transmembrane hematopoietic stem cell antigen: isolation, characterization, and molecular cloning. Blood 90:5013-21.

Mohr A. et al., (2005) Caspase-8L expression protects CD34+ hematopoietic progenitor cells and leukemic cells from CD95-mediated apoptosis. Oncogene. 24:2421-9.

Orlic D. et al., (2001) Mobilized bone marrow cells repair the infarcted heart, improving function and survival. Proc. Natl. Acad. Sci. USA 98:10344-9.

Park SM. et al., (2005) Nonapoptotic functions of FADD-binding death receptors and their signaling molecules. Curr Opin Cell Biol. 17:610-6.

Pearl-Yafe M. et al., (2006) The dual role of Fas-ligand as an injury effector and defense strategy in diabetes and islet transplantation. Bioessays. 28:211-22.

Peppercon et al., (2005) Quality of life among patients with Stage II and III breast carcinoma randomized to receive high-dose chemotherapy with autologous bone marrow support or intermediate-dose chemotherapy: results from Cancer and Leukemia Group B 9066. Cancer 104:1580-9.

Petersen BE. et al., (1999) Bone marrow as a potential source of hepatic oval cells. Science 284:1168-70.

Prockop DJ. et al, (2001) Isolation and characterization of rapidly self-renewing stem cells from cultures of human marrow stromal cells. Cytotherapy 3:393-6.

Rowley SD. et al., (1998) Isolation of CD34+ cells from blood stem cell components using the Baxter Isolex system. Bone Marrow Transplant 21:1253-62.

Saheki K. et al., (2000) Increased expression of Fas (APO-1, CD95) on CD34+ haematopoietic progenitor cells after allogeneic bone marrow transplantation. Br J Haematol. 109:447-52.

Sato T. et al., (1997) Expression and modulation of cellular receptors for interferon-gamma, tumour necrosis factor, and Fas on human bone marrow CD34+ cells. Br J Haematol. 97:356-65.

Simmons PJ and Torok-Strob B., (1991) Identification of stromal cell precursors in human bone marrow by a novel monoclonal antibody, STRO-1. Blood 1991;78:55-62.

Smith AG. (2001) Embryo-derived stem cells: of mice and men. Annu Rev Cell Dev Biol 17:435-62.

Katharine A. et al., (2002) Transduction of donor hematopoietic stem-progenitor cells with Fas ligand enhanced short-term engraftment in a murine model of allogeneic bone marrow transplantation. Blood. 100:3147-54.

Takenaka K. et al., (1996) In vitro expansion of hematopoietic progenitor cells induces functional expression of Fas antigen (CD95). Blood. 88:2871-7.

Testa U., (2004) Apoptotic mechanisms in the control of erythropoiesis. Leukemia. 18:1176-99.

Uchida N. et al., (2000) Direct isolation of human central nervous system stem cells. Proc. Natl. Acad. Sci. USA 97:14720-5.

Wajant H. et al., (2003) Non-apoptotic Fas signaling. Cytokine Growth Factor Rev. 14:53-66.

Ware CF., (2003) The TNF superfamily. Cytokine Growth Factor Rev. 14:181-4.

Wu W., (2001) Specific immunotherapy of experimental myasthenia gravis in vitro: the "guided missile" strategy. Cell Immunol 208:137-47.

Yang L. et al., (2005) IFN-gamma negatively modulates self-renewal of repopulating human hemopoietic stem cells. J Immunol. 174:752-7.

Yaniv I. et al., (2006) The tale of early hematopoietic cell seeding in the bone marrow niche. Stem Cells & Development. 15:4-16.

Yolcu ES. et al., (2002) Cell membrane modification for rapid display of proteins as a novel means of immunomodulation: FasL-decorated cells prevent islet graft rejection. Immunity 17:795-808.

Zauli G. and Secchiero P., (2006) The role of the TRAIL/TRAIL receptors system in hematopoiesis and endothelial cell biology. Cytokine Growth Factor Rev. 17:245-57.

* cited by examiner

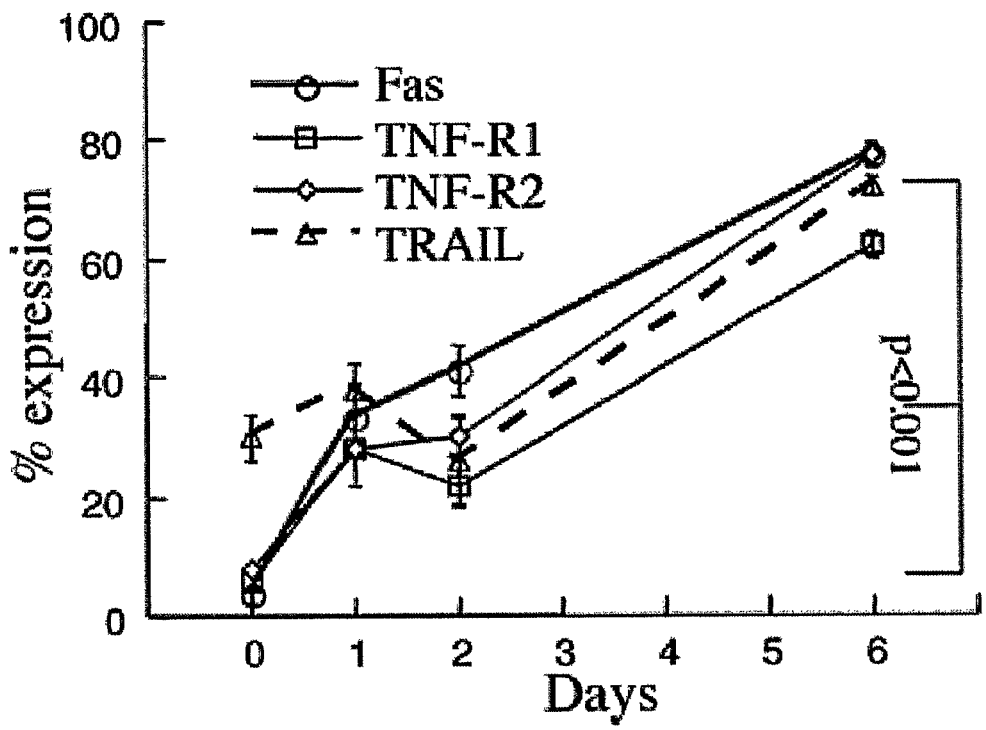
Fig. 3d
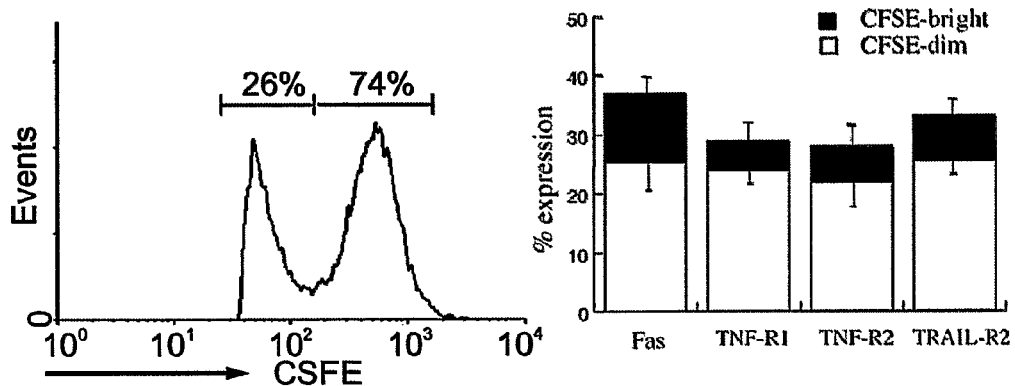
Fig. 3e
Fig. 3f

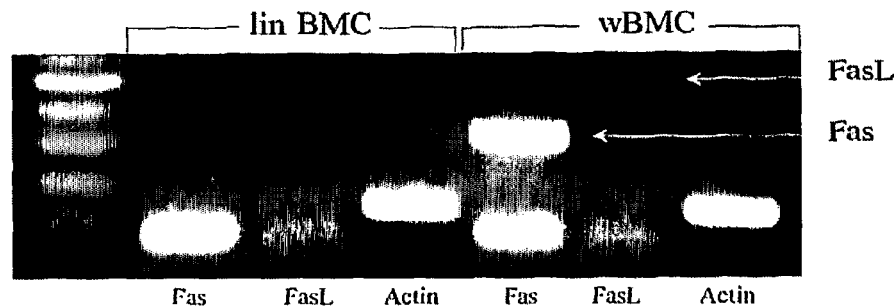
Fig. 4c
Fig. 4d
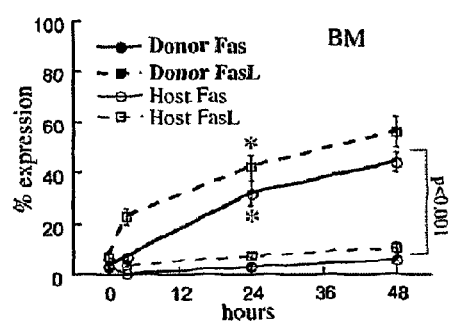
Fig. 4e
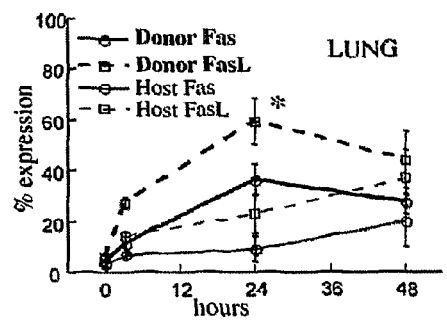
Fig. 4f
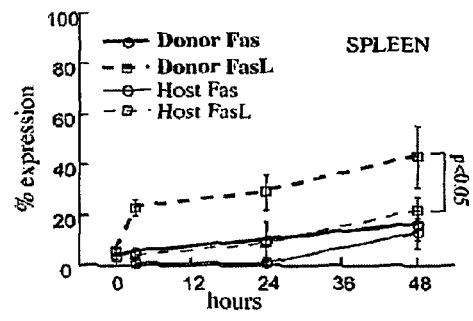
Fig. 4g
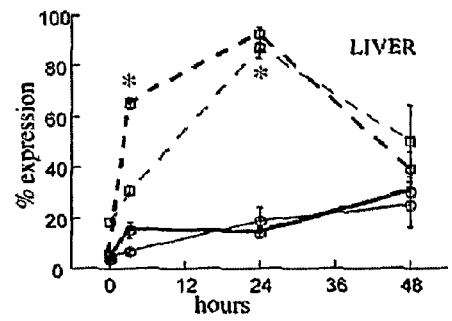

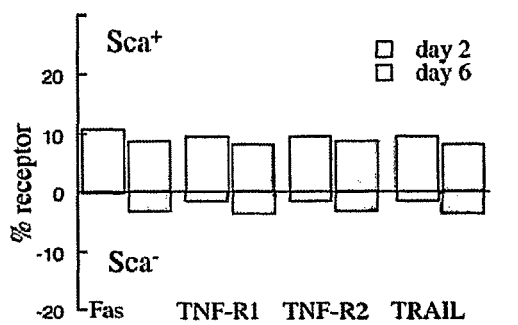
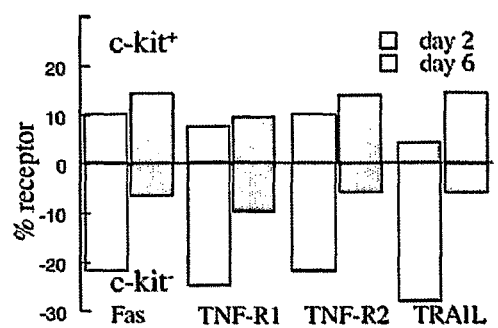
Fig. 5a
Fig. 5b
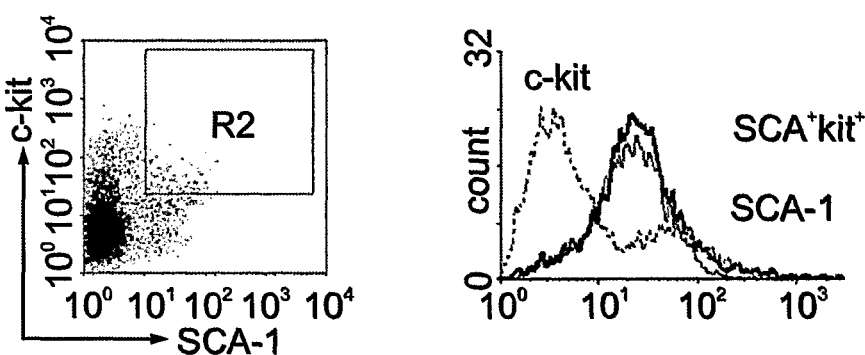
Fig. 5c
Fig. 5d

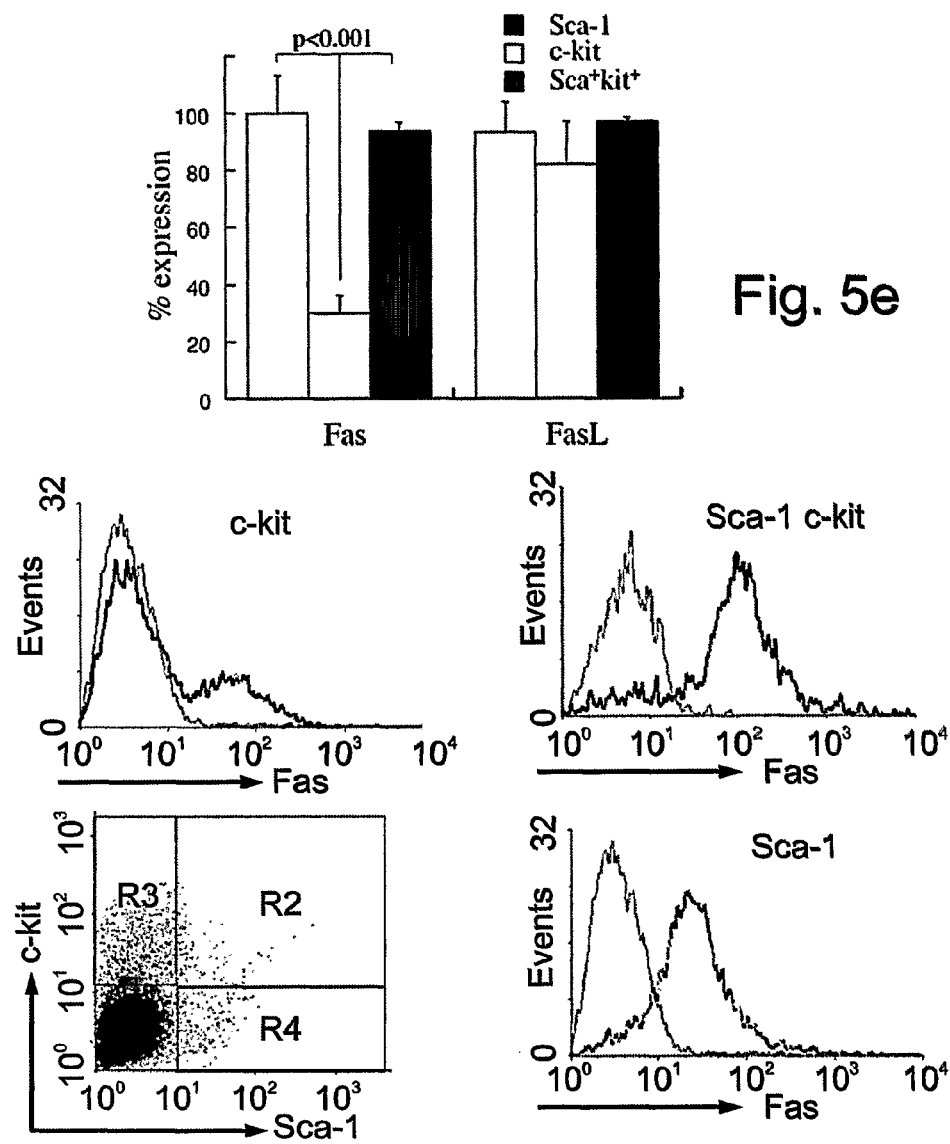
Fig. 5e
Fig. 5f
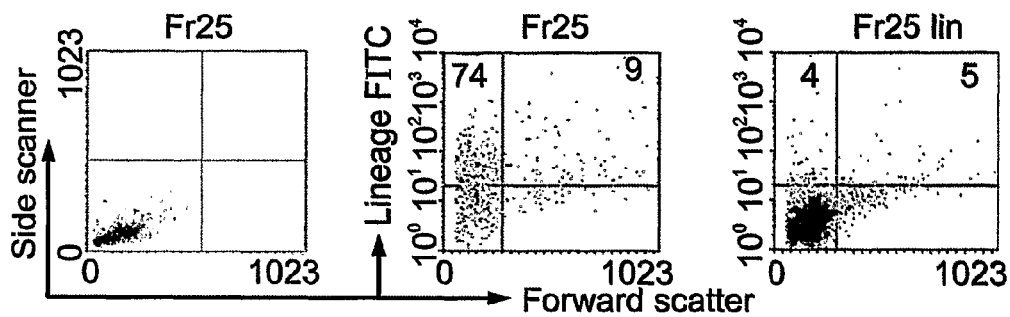
Fig. 5g

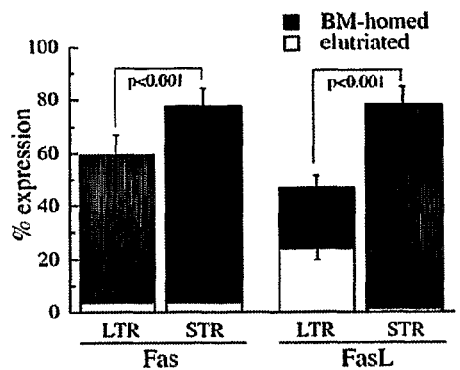
Fig. 5h
Fig. 6a
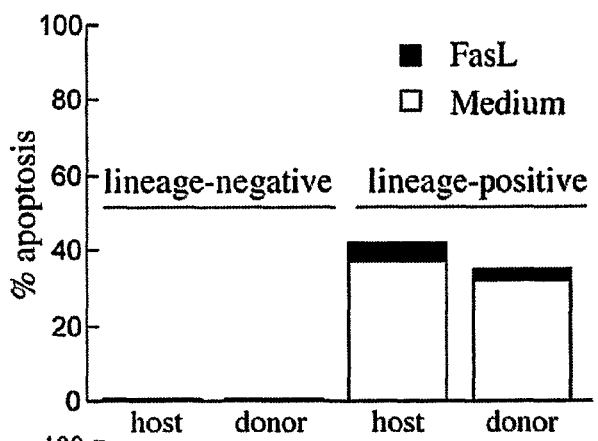
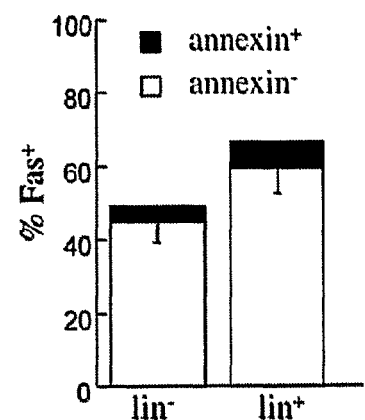
Fig. 6b
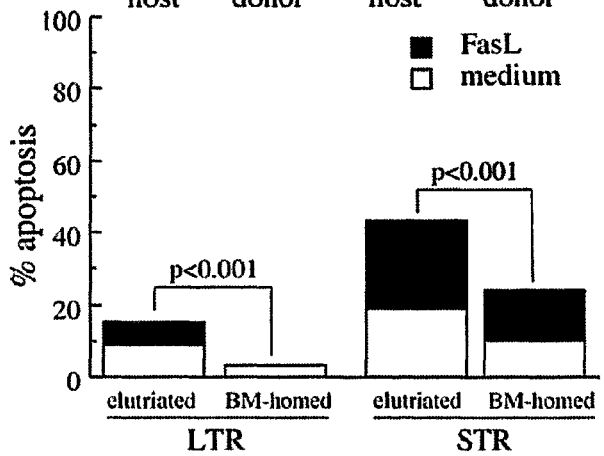
Fig. 6c
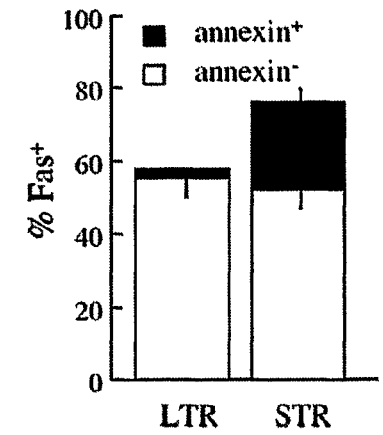
Fig. 6d Fig. 9a
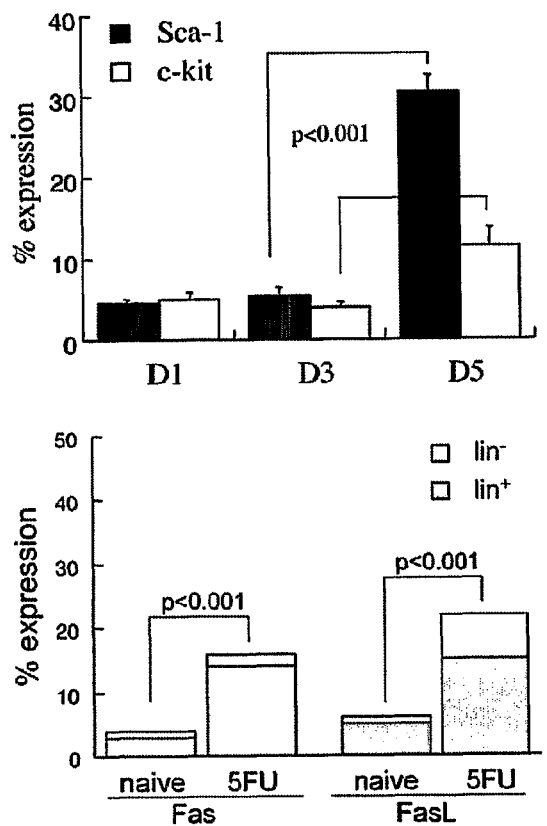
Fig. 9c
Fig. 9b
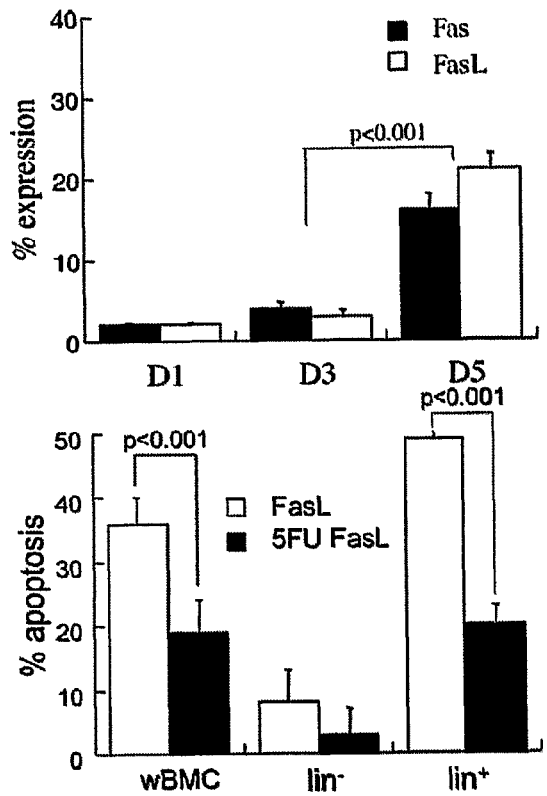
Fig. 9d
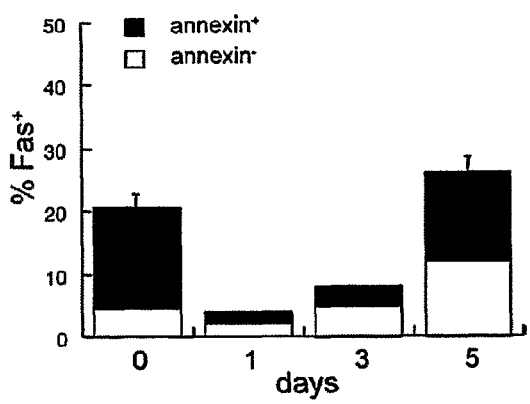
Fig. 9e
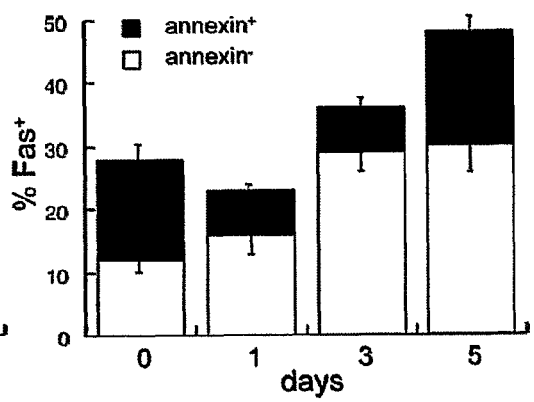
Fig. 9f

METHODS OF SELECTING STEM CELLS AND USES THEREOF

This Application is a national phase of, and claims priority from, PCT Application No. PCT/IL2007/000663, filed on May 31, 2007, which claims priority from U.S. Provisional Application Nos. 60/809,390, filed on May 31, 2006, and 60/840,013, filed on Aug. 25, 2006, all of which are hereby incorporated by reference as if fully set forth herein.

FIELD AND BACKGROUND OF THE INVENTION

The present invention relates to a method of selecting stem cells and uses thereof.

Stem cells have the unique property of being able to reconstitute populations of cells in the body. Typically, stem cells are divided into two main groups: adult stem cells and embryonic stem cells. The importance of technologies associated with expansion of stem cells, both of adult and/or embryonic derivation is illustrated by the numerous preclinical and clinical uses of these cells in treatment of a wide range of diseases.

Unlike all current treatments relying upon surgical intervention or drugs that modulate physiological activities, stem cells provide a replacement for dysfunctional or degenerating tissue. Using stem cells, replacement therapy could dramatically change the prognosis of many currently untreatable diseases, restore function of damaged organs and correct inborn disorders of metabolism and deficiencies.

The recent discoveries that adult stem cells derived from the bone marrow can give rise to non-hematopoietic tissues suggest that these cells may have greater differentiation potential than was previously assumed and open new frontiers for their therapeutic applications [Petersen, B. E. et al. Science 1999; 284:1168-1170; Brazelton, T. R. et al. Science 2000; 290:1775-1779; Krause, D. S. et al. Cell 2001; 105, 369-377].

Studies have shown that cord blood-derived stem cells are capable of repairing neurological damage caused by brain injuries and strokes [Lu D et al. Cell Transplant. 2002; 11:275-81] and are also capable of functional and morphological incorporation into animal heart tissue [Orlic, D. et al., Proc. Natl. Acad. Sci. USA 2001; 98:10344-9].

One of the earliest clinical uses of stem cells was for performing bone marrow transplants in patients with hematological malignancies in which hematopoietic stem cells derived from the donor bone marrow were administered into the recipient subsequent to providing the recipient with a sufficient dose of radiation and/or chemotherapy. This treatment ablates not only the malignant cells but also non-malignant cells. Endogenous hematopoietic cells rarely survive myeloablative radiation, and the stroma is severely damaged. In the aftermath of ablative injury, donor hematopoietic stem and progenitor cells (HSPC) find their way to the host bone marrow where they seed and engraft to reconstitute the immune-hematopoietic system. The prevalent sources of hematopoietic stem cells and progenitors include the bone marrow, umbilical cord blood and cells mobilized to the peripheral blood.

In addition to treatment of hematological malignancies, stem, progenitor and immune cells have been utilized in the context of therapy for solid tumors. Thus, for example, the use of autologous hematopoietic cell transplants combined with high dose chemo/radiotherapy for solid tumors has been extensively investigated for breast [Peppercorn, et al., 2005, Cancer 104:1580-1589]; colon [Leff, et al., J Clin Oncol 1986; 4:1586-1591], lung [Ziske, et al., Anticancer Res 2002; 22:3723-3726], nasopharyngeal cancer [Chen, et al., Jpn J Clin Oncol 2003; 33:331-335], and other types of cancers [Gratwohl, et al., Ann Oncol 2004; 15:653-660].

The identification of the type 1 transmembrane protein/adhesion molecule, the sialomucin CD34 as a marker of hematopoietic stem cells led to the use of CD34+ cell selection as a means of concentrating hematopoietic stem cell activity [Civin, et al., J Immunol 1984; 133:157-165]. Specifically, it was demonstrated that although bone marrow mononuclear cells contain approximately 1-4% $CD34^+$ cells, the administration of these cells, but not bone marrow depleted of $CD34^+$ cells, into lethally irradiated baboons led to hematopoietic reconstitution [Berenson, et al., J Clin Invest 1988; 81:951-955]. Similarly, CD133 has been considered as a marker of hematopoietic stem and progenitor cells [Kobari L, et al., J Hematother Stem Cell Res. 2001; 10:273-281]. Notably, the prevalence of stem cells in the bone marrow is much lower, in the order of 0.2-0.5%.

The above described method of isolating $CD34^+$ or $CD133^+$ cells results in a mixed cell population of stem and progenitor cells that includes all lineages and stages of lympho-hematopoietic stem and progenitor cells and some later precursor cells. This is disadvantageous, since it has been shown to be beneficial to isolate only the most primitive of the cells within the $CD34^+$ cell population [Askenasy N. et al., Current Stem Cell Research and Therapy 2006; 1:85-94]. Such positive selection procedures additionally suffer from some disadvantages including the presence of materials such as antibodies and/or magnetic beads on the $CD34^+$ cells, and damage to the cells resulting from the removal of these materials.

Furthermore, recent evidence suggests that expression of CD34 on the cell membrane does not always correlate with stem cell activity. It has been shown that in humans, there is a highly quiescent population of stem cells that lacks CD34 expression, but has full reconstituting capacity [Dao et al., Leukemia 2000; 14:773-776]. Hematopoietic progenitors have been repeatedly shown to be limited in their pluripotent differentiation potential, as compared to adult bone marrow and umbilical cord blood-derived stem cells that lack these phenotypic markers [Jang Y Y, et al., Nat Cell Biol. 2004; 6:532-539].

Accordingly, there is a continued interest in finding other methods to either replace or augment current methods of isolating cell populations that are enriched in stem cells and primitive progenitor cells.

Stem and progenitor cells are often required to perform differentiation tasks under extreme conditions of injury and inflammation. In this process, the expression and activation of death receptors in the developing hematopoietic cells have been attributed various functional roles, in particular negative regulation of differentiated cells, however the involvement of the death receptors in the proximal stages of HSPC function is unclear. The mechanisms by which hematopoietic reconstituting cells flourish in such devastated environment is of particular interest, as it may be used to improve the efficiency of engraftment.

There are more than 40 distinct ligand-receptor systems that are currently recognized as belonging to the tumor necrosis factor (TNF) superfamily. The majority of TNF ligands, most prominent Fas-ligand (FasL) and tumor necrosis factor-related apoptosis-inducing ligand (TRAIL), are synthesized as membrane-bound proteins and soluble forms are released by proteolysis. Various cell types store FasL in vesicles, which are excreted upon activation by various physiological stimuli. Within minutes from expression, FasL is cleaved from the cell surface by matrix metalloproteinases and accumulates as a soluble molecule. The soluble and membranous forms differ in their function with respect to apoptosis and immune regulation. Apoptosis is primarily mediated by the membrane-bound FasL, while the biology of the soluble isoform of FasL (sFasL) is complex, and includes apoptotic, anti-apoptotic, and chemotactic activities. Antiapoptotic (s)FasL competes with the membranous form for Fas binding, and is a chemotactic factor for neutrophils.

Expression of the Fas receptor in hematopoietic stem and progenitor cells (HSPC) is variable and changes along the lineage differentiation. Subpopulations of immature CD34+ CD38− human cells derived from the fetal liver, umbilical cord blood (UCB) and adult bone marrow (BM) were shown to express low (but detectable) levels of this receptors and other apoptosis mediating TNF receptors [Niho et al, Curr Opin Hematol. 1998; 5:163-165].

During hematopoietic cell differentiation, the Fas receptor is expressed in proliferating and differentiating progenitors, serving as a negative regulator of distal differentiation in all lineages [Gaur U, Aggarwal B B, Biochem Pharmacol. 2003; 66:1403-1408; Greil R, et al., Crit Rev Immunol. 2003; 23:301-322]. Such enhanced expression of Fas has been observed in cultured hematopoietic progenitors, and was associated with impaired viability and reduced clonogenesis following ex vivo cell exposure to cytokines, expansion and manipulation.

The TNF superfamily receptors and ligands have until presently been considered to be involved in increasing HSPC sensitivity to apoptotic signals under various experimental conditions. It was assumed that the excessive expression of Fas in HSPC exposed to injury signals following transplantation promotes the execution of apoptosis in donor cells and is involved in suppression of donor cell activity. Ex vivo incubation of human CD34+ HSPC and murine c-ki+lin− SCA-1+ (KLS) HSPC with TNF-α was associated with increased expression of the Fas receptor and resulted in deficient homing and engraftment [Bryder D, J Exp Med 2001; 194: 941-952; Dybedal I, Blood. 2003; 102:118-126]. All these detrimental effects were efficiently induced by activating anti-Fas antibodies and were reversed by blocking anti-Fas antibodies and soluble Fas-ligand. In corroboration with the negative role attributed to the Fas receptor in engraftment of HSPC, marrow hypoplasia caused by graft versus host disease was ameliorated by injection of FasL-defective cells [Iwasaki T, et al., Cell Immunol. 1999; 197:30-38].

Civin et al [U.S. Appl. No. 20040131599] teach a method for suppressing the immune response of a recipient mammal to a donor hematopoietic stem cell graft by expressing a recombinant FasL gene in donor hematopoietic stem cells. The positive role of FasL in this context was attributed to the killing of reactive T lymphocytes of the host to ameliorate allorejection, and of the donor to ameliorate graft versus host disease.

Shirwan et al [U.S. Appl. No. 20040018170] teach a method for treating conditions which are alleviated by the apoptosis of activated lymphocytes. Specifically Shirwan et al disclose the use of proteins, for example stable tetramers of FasL, in order to enhance the efficiency of activation of death receptors in activated 5 lymphocytes.

Both methods use ligands for death receptors to eliminate reactive immune cells through activation-induced cell death [Cohen J J, Duke R C. Ann Rev Immunol. 1992; 10:267-293].

However, neither Civin et al, nor Shirwan et al suggest nor allude to selection of stem cells or purification of stem cell populations prior to transplant.

Josefsen et al., [Exp Hematol. 1999; 27:1451-1459] teach promotion of CD34+ CD38− cell viability and enhancement of cytokine induced clonogenicity by addition of soluble FasL. Similar results were obtained with CD34++CD38− fetal liver cells [Barcena et al., Exp Hematol. 1999,27:1428-1439]. In this case, soluble FasL was used to inhibit apoptosis mediated by activation (trimerization) of the Fas receptor [Askenasy N, et al., Blood. 2005; 105:1396-404], which is expressed in a significant fraction of human cells transplanted in human subjects [Saheki K, et al., Br J Haematol. 2000; 109:447-452] and in murine models of xenotransplantation [Dybedal I, et al., Blood. 2003; 102:118-126]. However, the use of Fas-L as an agent to select for stem cells was not suggested.

SUMMARY OF THE INVENTION

According to one aspect of the present invention there is provided a method of selecting stem cells from a heterogeneous population of cells, the method comprising contacting the population of cells with an apoptosis inducing agent under conditions which are apoptotic to non-stem cells and non-apoptotic to stem cells, thereby selecting the stem cells from the heterogeneous population of cells.

According to another aspect of the present invention there is provided a method of transplanting selected stem cells into a host, the method comprising:

(a) contacting stem cells of a heterogeneous population of cells with an apoptosis inducing agent under conditions that are apoptotic to non-stem cells and non-apoptotic to stem cells to thereby select stem cells; and (b) transplanting the selected stem cells into a host, thereby transplanting the selected stem cells.

According to further features in the described preferred embodiments, the method further comprises isolating the selected stem cells following step (a) and prior to step (b).

According to yet another aspect of the present invention there is provided a method of differentiating stem cells, the method comprising:

(a) contacting stem cells of a heterogeneous population of cells with an apoptosis inducing agent under conditions that are apoptotic to non-stem cells and non-apoptotic to stem cells to thereby select stem cells; and (b) inducing differentiation of the selected stem cells, thereby differentiating stem cells.

According to further features in preferred embodiments of the invention described below, the stem cells are selected from the group consisting of umbilical cord blood stem cells, mobilized peripheral blood stem cells, bone marrow stem cells and neural stem cells.

According to still further features in the described preferred embodiments, the stem cells are bone marrow stem cells.

According to still further features in the described preferred embodiments, the bone marrow stem cells are hematopoietic stem cells.

According to still further features in the described preferred embodiments, the, method further comprises modifying the stem cells prior to the contacting so as to generate modified stem cells.

According to still further features in the described preferred embodiments, the method further comprises purifying the stem cells prior to the contacting so as to generate purified stem cells.

According to still further features in the described preferred embodiments, the method further comprises expanding the stem cells prior to the contacting so as to generate expanded stem cells.

According to still further features in the described preferred embodiments, the bone marrow stem cells are mesenchymal stem cells.

According to still further features in the described preferred embodiments, the stem cells are adult stem cells.

According to still further features in the described preferred embodiments, the stem cells are embryonic stem cells.

According to still further features in the described preferred embodiments, the apoptosis inducing agent is selected from the group consisting of TNF-α, FasL, Trail and Tweak.

According to still further features in the described preferred embodiments, the apoptosis inducing agent is FasL.

According to still further features in the described preferred embodiments, the FasL is conjugated to a surface.

According to still further features in the described preferred embodiments, the FasL is non-cleavable.

According to still further features in the described preferred embodiments, the method further comprises up-regulating expression of an apoptosis receptor on the heterogeneous population of cells prior to the contacting.

According to still further features in the described preferred embodiments, the apoptosis receptor is selected from the group of receptors consisting of a Fas receptor, a TNF-α receptor, a Tweak receptor and a Trail receptor.

According to still further features in the described preferred embodiments, the up-regulating expression of the apoptosis receptor is effected by contacting the heterogeneous population of cells with Interferon γ or TNF-α.

According to still further features in the described preferred embodiments, the heterogeneous population of cells does not comprise immune activated T lymphocytes.

According to still further features in the described preferred embodiments, the heterogeneous population of cells comprises lineage positive cells.

According to still further features in the described preferred embodiments, the lineage positive cells are selected from the group consisting of granulocytes, macrophages, natural killer cells, erythroblasts, antigen presenting cells, myeloid cells, lymphoid cells, and megakaryocytes.

According to still further features in the described preferred embodiments, the heterogeneous population of cells comprises apoptosis sensitive malignant cells.

According to still further features in the described preferred embodiments, the method further comprises isolating the stem cells following the contacting.

According to still further features in the described preferred embodiments, the stem cells are autologous to the host.

According to still further features in the described preferred embodiments, the stem cells are syngeneic to the host.

According to still further features in the described preferred embodiments, the stem cells are allogeneic to the host.

According to still further features in the described preferred embodiments, the stem cells are xenogeneic to the host.

According to still further features in the described preferred embodiments, the inducing differentiation is effected by expressing a gene product in the stem cells.

According to still further features in the described preferred embodiments, the gene product is a polypeptide.

According to still further features in the described preferred embodiments, the gene product is a polynucleotide.

The present invention successfully addresses the shortcomings of the presently known configurations by providing a novel method of selecting for stem cells based on their insensitivity to apoptotic signals.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fudamental understanding of the invention, the description taken with the drawings making apparent to those skilled in the art how the several forms of the invention may be embodied in practice.

In the drawings:

FIGS. 3A-H illustrate expression of death receptors in bone marrow-homed donor cells. A. Whole BMC express low levels of TNF family death receptors, while ~30% of the lin– BMC are positive for TRAIL-R2. B. Residual bone marrow cells express low levels of death receptors after total body irradiation (850 rad), independent of cell transplantation (n=5). C. Fas, TNF-R1 and TNF-R2 are markedly upregulated in donor cells that home successfully to the bone marrow of irradiated syngeneic hosts. Data represent means±SD of expression at 48 hours post-transplantation (n=5). D. Expression of the death receptors progressively increased in donor cells during the first days after transplantation (n=4). E. Lin$^-$ BMC (>90% pure) pre-labeled with CFSE were transplanted into irradiated syngeneic recipients (850 rad TBI), and the bone marrow-homed cells were analyzed after 48 hours for CFSE dilution (n=7). Approximately 25% of the cells cycled fast, as determined by CFSE dilution (CFSE$^{dim}$). F. The death receptors were upregulated (n=5) primarily in fast cycling cells (CFSE$^{dim}$), with expression in a smaller fraction of slow cycling cells (CFSE$^{bright}$). G. Approximately one fifth of the donor lin$^-$ BMC expressed lineage markers within 48 hours after transplantation, indicative of early differentiation (n=11). H. Death receptors were upregulated predominantly in early differentiating cells (n=8).

FIGS. 4A-G illustrate the dynamic expression of Fas receptor and ligand. A. Mice conditioned with 850 rad total body irradiation (TBI) were injected with 1-2×10$^7$ allogeneic lin$^-$ BMC (H2K$^d$→H2K$^b$). After 48 hours the bone marrow of the recipient mice was harvested and the expression of Fas and FasL were determined in reference to the donor-host origin and lineage marker expression (n=8). B. Fas and FasL are jointly co-expressed by the same donor cells. The demonstrative readout was characteristic of multiple experiments (n=29). C. Naïve lin$^-$ and whole (w)BMC were assayed by RT-PCR for the presence of mRNA encoding Fas and FasL. Data are representative of 3 independent experiments showing similar results. D-G. The patterns of Fas and FasL expression were determined by flow cytometry after syngeneic transplants (CD45.1→CD45.2) of lin$^-$ BMC into irradiated mice (850 rad TBI) in (D) bone marrow, (E) lung, (F) spleen and (G) liver, in parallel to the expression of these molecules in the parenchymal cells of the respective organs (n=5).

FIGS. 5A-H illustrate expression of death receptors in hematopoietic stem and progenitor cells. A-B. Bone marrow-homed cells were analyzed for expression of death receptors in reference to the HSPC markers (A) Sca-1 and (B) c-kit, at 2 and 6 days after syngeneic transplants of CFSE$^+$lin$^-$ BMC (n=8). Expression of HSPC markers is expressed as a fraction of the cells positive for the death receptors. C. All candidate hematopoietic HSPC defined as lin$^-$Sca-1$^+$c-kit$^+$ that home to the bone marrow of irradiated syngeneic hosts express the death receptors (n=8). D. Representative readout of TNF-R1 expression in lin$^-$Sca-1$^+$c-kit$^+$ HSPC. E. While Fas expression was found in ~30% of the c-kit$^+$ cells, FasL was expressed by the majority of this subset, and virtually all lin$^-$Sca-1$^+$ and lin$^-$Sca-1$^+$c-kit$^+$ cells (n=7). F. Representative readouts of Fas expression in the Sca-1$^+$ and c-kit$^+$ subsets of bone marrow-homed CFSE$^+$lin$^-$ cells. G. Small sized cells were isolated by counterflow elutriation at a flow rate of 25 ml/min, were analyzed for lineage marker expression and were lineage depleted to yield a >90% lineage-negative subset of Fr25 lin$^-$ cells (LTR). The data are representative of 7 independent experiments. H. STR cells were collected after elutriation, in the rotor off position. LTR and STR cells were transplanted into syngeneic irradiated hosts (CD45.2→CD45.1), and were harvested after two days for analysis of Fas and FasL expression. The data represent means of 5 independent experiments.

FIGS. 6A-H illustrate the resistance of hematopoietic reconstituting cells to apoptosis. A. Bone marrow-homed cells were harvested 2 days after syngeneic transplants (CD45.1→CD45.2), and submitted to an apoptotic challenge with FasL protein (250 ng/ml) for 18 hours (n=6). Donor and host origin of the cells was determined in parallel to lineage marker expression, death (7AAD) and apoptosis (annexin-V). Cells incubated in (FasL-free) medium served as controls. B. Apoptotic death (annexin-V) was measured in reference to Fas receptor expression in lineage-negative (lin$^-$) and lineage positive (lin$^+$) markers by gating on the donor cells (n=5). C. Elutriated and day-2 bone marrow-homed Fr25 lin$^-$ (LTR) and STR cells were incubated in supporting medium and were challenged with 250 ng/ml FasL protein for 18 hours in vitro (n=5). D. Apoptotic death was measured in reference to Fas expression in day-2 bone marrow-homed LTR and STR cells in three independent experiments. E. Apoptotic death was determined in day-2 bone marrow-homed cells positive for the Fas, TNF and TRAIL receptors after their exposure to an apoptotic challenge with 250 ng/ml FasL protein in vitro. F. Sublethally-irradiated (850 rad) recipients were transplanted with 5×10$^5$ syngeneic cells (CD45.1→CD45.2), either fresh (n=10) or after preincubation for 24 hours (n=12) with FasL protein. Chimerism was determined in peripheral blood lymphocytes by flow cytometry after 3 weeks. G. Pre-incubation with FasL protein did not affect short-term and long-term engraftment (n=8). H. Survival of myeloablated mice (950 rad) transplanted with 1.5×10$^5$ naïve and FasL-pretreated BMC from syngeneic (CD45.2→CD45.1) and allogeneic (H2k$^b$→H2k$^d$) donors (n=20).

FIGS. 9A-F illustrate the function of death receptors under 5FU-induced stress hematopoiesis. Mice were injected with 10 µg/g 5FU and their bone marrow cells were harvested for analysis after 1, 3 and 5 days (n=6). A. Expression of cell surface markers characteristic of candidate murine HSPC Sca-1 and c-kit. B. Expression of Fas and FasL. C. Expression of Fas and FasL in reference to lineage marker expression in naïve BMC and cells 5 days after 5FU administration. D. Naïve BMC and cells harvested 5 days after 5FU administration were incubated ($5\times10^6$ cells/ml) for 24 hours in $\alpha$-MEM culture medium supplemented with StemPro Nutrient Supplement, 2 mM L-glutamine, 50 µM 2$\beta$-Mercatoethanol and were challenged with 250 ng/ml FasL protein. Apoptosis was determined by annexin-V incorporation in reference to lineage marker expression (n=5). E. BMC harvested on days 1, 3 and 5 after 5FU administration were incubated for 24 hours in medium for determination of viability (annexin$^-$) and apoptosis (annexin$^+$) within the fraction of Fas$^+$ cells. E. Cells incubated under same conditions were submitted to the apoptotic challenge with 250 ng/ml FasL protein. F. Apoptosis (annexin$^+$) was plotted against Fas receptor expression, summarizing data from 5 mice.

DESCRIPTION OF THE PREFERRED EMBODIMENTS

The present invention is of a method of selecting stem cells and purging heterogeneous populations of cells from non-stem cells.

The principles and operation of the selection method of the present invention may be better understood with reference to the examples and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The myriad of uses of stem cells in the treatment of a wide range of diseases dictates that it is of great importance that large numbers of such cells be identified and purified.

Within the hematopoietic system, stem cells are typically identified on the basis of their cell surface phenotype, e.g. CD34$^+$. However, ample evidence suggests that expression of CD34 on the cell membrane does not always correlate with stem cell activity. Other strategies that have been employed to detect and purify hematopoietic stem cells (HSCs) are based on the staining patterns of fluorescent dyes. Decreased staining with the vital fluorescent dyes Hoechst 33342 (a bis-benzimidazole that binds to adenine-thymine-rich regions of the minor groove of DNA) and rhodamine 123 (which preferentially accumulates in active mitochondria) has long been used in flow cytometry experiments to enrich for HSCs.

The use of the above mentioned selection procedures tend towards selection of stem cells or early progenitor cells with a bias towards the hematopoietic phenotype.

Whilst investigating the engraftment potential of hematopoietic cells, the present inventors detected an up-regulation of expression of death receptors in donor cells early after transplantation (FIGS. 3A-B), induced at least in part by factors (chemokines and cytokines) released as a result of radiation-injury.

Figure 1A:
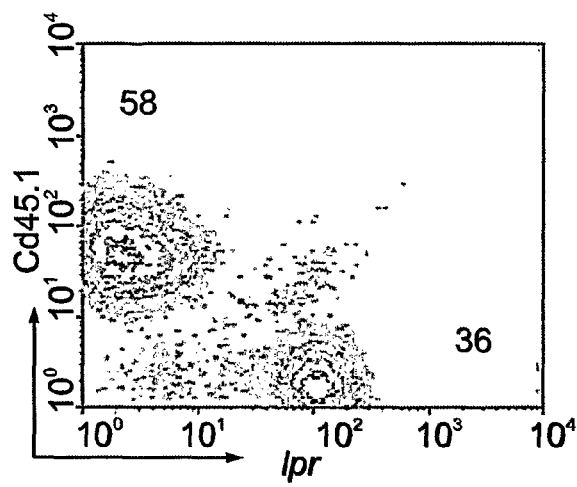
FIGS. 1A-H illustrate the functional involvement of the Fas/FasL interaction in syngeneic hematopoietic cell engraftment. A. Myelaoblated (950 rad) GFP mice (CD45.2$^+$GFP$^+$) were transplanted with a 1;1 mixture of 5×10$^5$ lin$^-$ BMC from syngeneic wild type (CD45.1$^+$GFP$^-$) and Fas-defective (lpr) donors (CD45.2$^+$GFP$^-$). Hematopoietic chimerism was measured in the peripheral blood at 3 weeks post-transplantation to compare the wt (CD45.1) and lpr (CD45.2) donor cell (GFP$^-$) engraftment (n=16). B. Syngeneic transplants of 5×10$^5$ lin– BMC into sublethally irradiated (850 rad) recipients (CD45.1→CD45.2). Engraftment at 3 weeks was deficient when lpr cells were transplanted into wild type (wt) recipients (n=8) and when wt cells were transplanted into lpr recipients (n=10). C. Deficient engraftment of gld cells in wt recipients (n=8) and of wt cells in gld recipients (n=11) was efficiently reversed by expression of ectopic FasL protein on the surface of donor cells via biotinylation (n=9). D. Demonstrative differences in peripheral blood chimerism at 3 weeks after syngeneic transplants of wt cells coated with FasL protein. E. Expression of FasL in 5×10$^5$ lin$^-$ BMC transplanted into syngeneic lpr recipients (CD45.1→CD45.2) had no significant effect on engraftment at 3 weeks (n=6). F. Transplantation of 10$^7$ whole BMC from GFP donors into myeloablated lpr recipients resulted in full donor (GFP$^+$) chimerism in bone marrow at 6 weeks post transplantation (n=8). G. Stromal cultures of the GFP/lpr chimeras were predominantly of the lpr (GFP$^-$) host phenotype after gating out CD45$^+$ and CD11c$^+$ cells. The data are representative of cultures from 5 transplanted mice. H. Full GFP/lpr chimeras (Fas$^+$GFP$^+$ BMC and Fas$^-$GFP$^-$ stroma) served as recipients of naïve and FasL-coated lin$^-$ BMC from syngeneic CD45.1 mice (n=6). Chimerism was unaffected by FasL expression, similar to the transplants in lpr mice, suggesting that stroma was targeted by donor cell FasL.
Figure 1B:
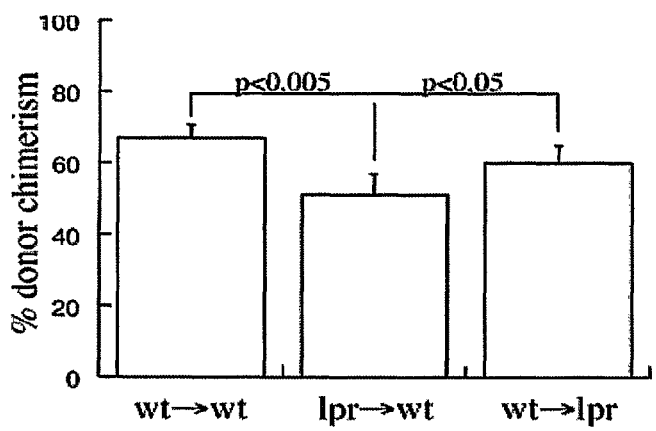

The present inventors attributed a positive role for the induced death receptors in the early stages of hematopoietic cell engraftment since they noted a decrease in engraftment potential of hematopoietic stem cells in Fas-defective (lpr) and FasL-defective (gld) mice (FIGS. 1A-B). Furthermore, the inventors showed that a transient display of ectopic FasL protein improved both syngeneic (FIGS. 1C-D) and allogeneic (FIGS. 2A-E) cell engraftment of hematopoietic stem cells.

Figure 6F:
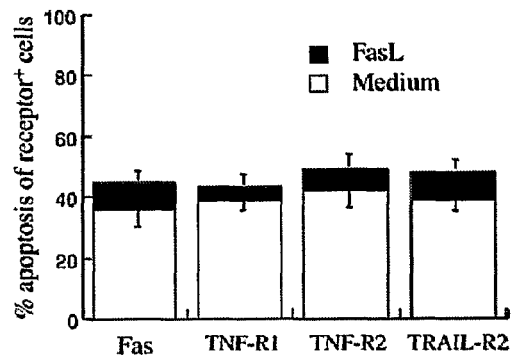
Figure 6F:
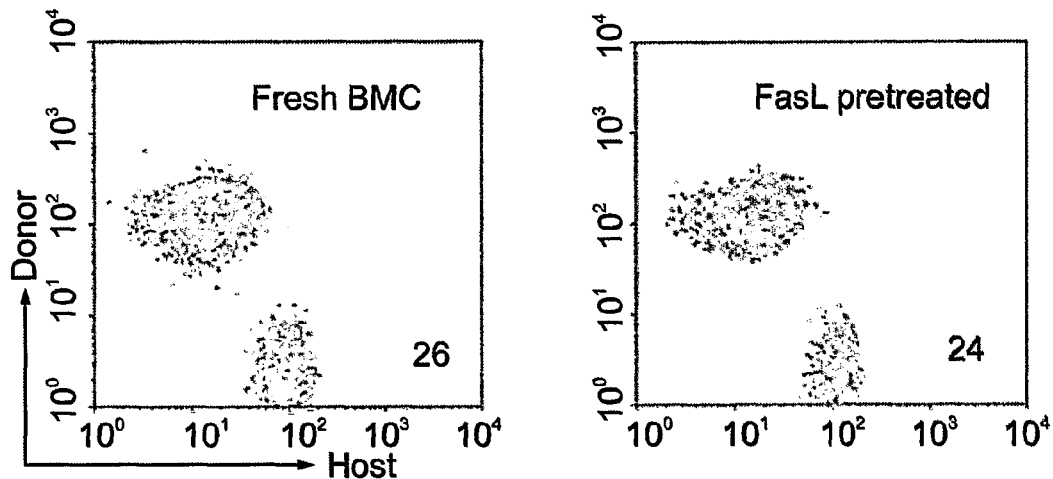

In addition, the present inventors showed that only the most primitive progenitors up-regulated death receptors soon after transplantation, and maintain this expression over the next days (FIGS. 5A-H). Remarkably, even though these cells showed a high level of death receptors, they remained resistant to apoptotic signals (FIGS. 6A-B).

The present inventors concluded from these results that in progenitors with hematopoietic reconstituting potential, the death receptors expressed thereon do not mediate apoptotic signals. The very same receptors that mediate death in distal stages of differentiation and in somatic cells, mediate trophic signals in most primitive hematopoietic stem and progenitor cells.

Figure 7A:
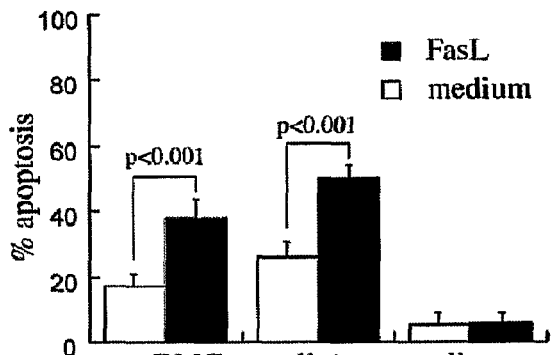
FIGS. 7A-K illustrate the Sensitivity of hematopoietic stem cells to Fas-mediated apoptosis. 5×10$^6$ cells/ml were incubated for variable periods in α-MEM culture medium supplemented with StemPro Nutrient Supplement, 2 mM L-glutamine, 50 μM 2β-Mercatoethanol. A. Whole BMC were incubated for 24 hours in culture medium with and without 250 ng/ml FasL protein. Cell death and apoptosis were determined by 7AAD and annexin-V incorporation respectively, and lineage markers were determined with a cocktail of antibodies. The data summarize 5 independent experiments. B. Analysis of the lineages of BMC that underwent apoptosis in response to incubation with 250 ng/ml FasL protein revealed susceptibility to apoptosis of all major subsets of lineage-positive BMC: granulocytes (GR-1), macrophages (Mac-1), erythroid (Ter), B lymphocytes (B220) and T lymphocytes (CD5). The data represent percent values for the entire wBMC population in 6 independent experiments. C. Apoptotic (annexin$^+$) and viable cells (annexin$^-$) were determined as a function of Fas receptor expression in reference to lineage marker expression (lin$^-$ and lin$^+$) within naïve whole BMC after incubation with and without 250 ng/ml FasL protein for 24 hours (n=7 independent incubations). The horizontal bar represents Fas expression at the onset of incubation. D. Lin$^-$ BMC were incubated for 24 hours with and without the addition of 10 ng/ml stem cell factor (SCF), 100 ng/ml thrombopoietin (TPO) and 75 ng/ml FasL protein. Apoptosis (annexin$^+$) and viability (annexin$^-$) were measured in reference to Fas receptor expression (n=3 independent incubation). E-J. $10^7$ wBMC were incubated for 3 days in medium supplemented with 50 ng/ml TNF-$\alpha$ (TNF), during the last day with 250 ng/ml FasL protein (FasL) and the combination of these (TNF+FasL). Apoptosis was determined by annexin incorporation in reference to expression of Fas and TNF receptors (n=4 independent incubations). E. Number of viable lin$^-$ and lin$^+$ cells after incubation in medium. F. Percent apoptosis of receptor-positive cells incubated in medium. G. Number of viable lin$^-$ and lin$^+$ cells after incubation in medium supplemented with SCF and TPO. H. Percent apoptosis of receptor-positive cells incubated with SCF and TPO. I. Number of viable lin$^-$ and lin$^+$ cells after incubation in medium supplemented with SCF, TPO and interleukin (IL)-3. J. Percent apoptosis of receptor-positive cells incubated with SCF, TPO and IL-3. K. Increase in percent lin– cells after 5 days of incubation of wBMC in medium and in medium supplemented with SCF, TPO and IL-3 (n=3 independent incubations).
Figure 7B:
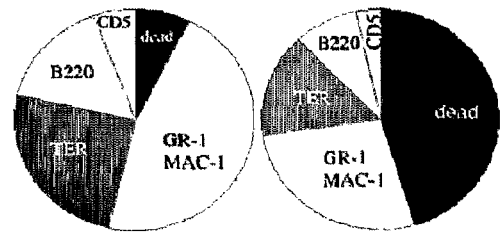
Figure 7C:
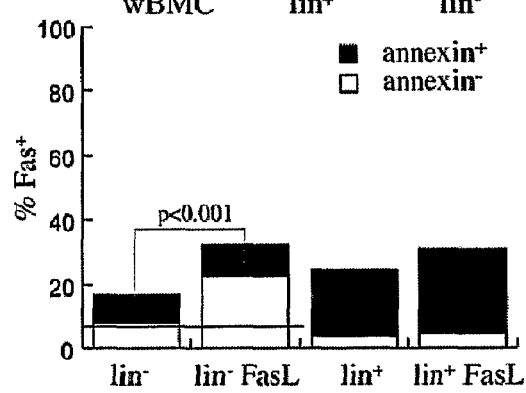
Figure 7D:
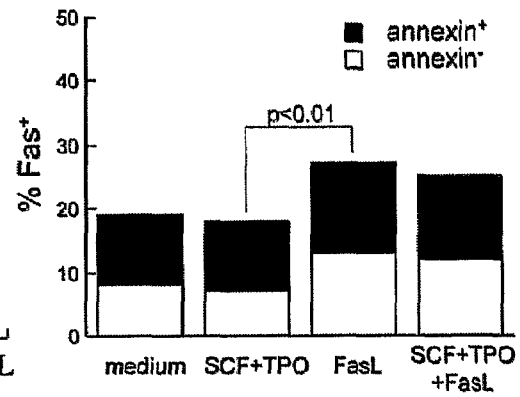

Whilst reducing the present invention to practice, the present inventors showed that pre-incubation of naïve (i.e. non-modified, for example to express an apoptotic mediator) bone marrow cells with pro-apoptotic ligands such as FasL, stimulated the expression of Fas (FIG. 7C) and further showed that a large proportion of these cells were insensitive to apoptosis (FIG. 7D).

The present invention seeks to exploit this naturally occurring phenomenon for the selection and enrichment of stem cells in a heterogeneous cell population. Since the present inventors have shown that only the most primitive of progenitor cells are immune to pro-apoptotic signals, the present invention leads to the generation of cell populations with a higher plasticity than those generated by separation according to expression of cell markers such as CD34 and therefore unlike CD34+ cells, are not biased towards a hematopoietic lineage. Accordingly, the present inventors propose selection of stem and progenitor cells using a functional characteristic: the insensitivity of these cells to apoptotic signals signaled through cell surface death receptors.

The present invention can be used to provide ex-vivo populations of stem cells, which can be used for applications in hematopoietic cell transplantations, and in generation of stem cells suitable for genetic manipulations, which may be used for cellular gene therapy. Additional applications may include, but are not limited to, adoptive immunotherapy, treatments for multiple diseases, such as, for example, β-hemoglobinopathia, implantation of stem cells in an in vivo differentiation and trans-differentiation settings, and ex vivo tissue engineering in differentiation and trans-differentiation settings.

Thus, according to one aspect of the present invention, there is provided an ex vivo method of selecting stem cells from a heterogeneous population of cells. The method comprises contacting the population of cells with an apoptosis inducing agent under conditions which are apoptotic to non-stem cells and non-apoptotic to stem cells.

As used herein, the term "selecting" refers to a method of distinguishing between the stem cells of the present invention as defined herein below and non-stem cells. Since, the method of the present invention inevitably leads to the death of the non-stem cells, as further described herein below, the selecting process leads to the enriching of stem cells of the present invention by the purging of non-stem cells.

The phrase "stem cell" as used herein refers to non-terminally differentiated cells that express (or may be induced to express) an apoptotic mediator but which are resistant to an apoptotic signal. Thus, included under the definition of stem cells, are early progenitor cells, which are somewhat more differentiated than stem cells, yet have been shown by the present inventors to be resistant to apoptotic signals despite expressing apoptotic receptors. The stem cells selected according to the method of the present invention may be characterized by functional properties. Thus for example, the present inventors have shown that the stem cells selected according to the method of the present invention comprise enhanced engraftment properties compared to stem cells selected according to other prior art methods.

The stem cells of the present invention may be derived from the umbilical cord blood, from peripheral blood, from the bone marrow (e.g. mesenchymal stem cell, hematopoietic stem cells) or any adult tissue including, but not limited to brain, liver and muscle. In addition the stem cells may be embryonic stem cells and derivatives thereof.

Embryonic stem cells and methods of their retrieval are well known in the art and are described, for example, in Trounson A O (Reprod Fertil Dev 2001; 13:523), Roach M L (Methods Mol Biol 2002; 185:1), and Smith A G (Annu Rev Cell Dev Biol 2001; 17:435). Adult stem cells are stem cells, which are derived from tissues of adults and are also well known in the art. Methods of isolating or enriching for adult stem cells are described in, for example, Miraglia, S. et al. Blood 1997; 90:5013; Uchida, N. et al. Proc. Natl. Acad. Sci. USA 2000; 97:14720; Simmons, P. J. et al. Blood 1991; 78:55; Prockop D J Cytotherapy 2001; 3:393, Bohmer R M et al. Fetal Diagn Ther 2002; 17:83) and Rowley S D et al. Bone Marrow Transplant 1998; 21:1253; Stem Cell Biology Daniel R. Marshak (Editor) Richard L. Gardner (Editor), Publisher: Cold Spring Harbor Laboratory Press, (2001) and Hematopoietic Stem Cell Transplantation. Anthony D. Ho (Editor) Richard Champlin (Editor), Publisher: Marcel Dekker (2000).

According to this aspect of the present invention, the stem cells are selected from a heterogeneous population of cells.

As used herein, the phrase "heterogeneous population of cells" refers to mixture of at least two types of cells, one type being the stem cells as defined above and the other being apoptosis-sensitive. The heterogeneous population of cells may be derived from any organism or organisms, preferably mammalian and even more preferably human.

According to one embodiment, the heterogeneous population of cells comprises a mixture of lineage positive cells and stem cells. In this instance, the method of the present invention may be used to perform lineage depletion.

As used herein, the phrase "lineage positive cells" refers to cells that are committed towards a specific cell lineage, such as committed progenitors and other further differentiated cells. Typically lineage positive cells express lineage differentiated markers, examples of which include, but are not limited to CD3, CD61, CD19, CD33, CD14, CD15 and/or CD4.

Examples of lineage positive cells which may be depleted according to the selection method of the present invention include, but are not limited to B and T lymphocytes (both mature and premature), granulocytes, macrophages, natural killer cells, erythroblasts, antigen presenting cells, myeloid cells, lymphoid cells and megakaryocytic cells. Preferably, the T lymphocytes are not immune activated T lymphocytes i.e. T cell receptor activated T lymphocytes.

According to another embodiment the heterogeneous population of cells comprises a mixture of stem cells and apoptosis-sensitive malignant cells. Thus, the method of the present invention may be used to purge the heterogeneous population of malignant cells.

The heterogeneous population of cells may be enriched for stem cells prior to the selection method of the present invention using techniques known in the art such as by FACS, wherein the stem cells are defined as being $CD34^+$ or any other marker, by exclusion of Rhodamine 123 and Hoescht, by counterflow centrifugal elutriation and by lineage depletion to obtain a population of small blasts.

The heterogeneous population of cells may be comprised in a tissue (e.g. bone marrow) or part thereof, in an aggregate, in a single cell suspension or as part of a primary culture or cellular sample, so long as they are accessible to the pro-apoptotic agents of the present invention.

The heterogeneous population of cells may be modified prior to the selection method of the present invention, although preferably the modification process does not affect the resistance of the stem cells to an apoptotic agent such that they can no longer be selected according to the method of the present invention. Thus, for example, the heterogeneous population of cells may be genetically modified to express a molecule of interest.

Alternatively, or additionally, the heterogeneous population of cells may be expanded. Preferably, the culture conditions used for expansion of the heterogeneous population of cells leads to a net gain in stem cells of the present invention and does not cause the stem cells to become sensitive to apoptosis.

Methods of ex-vivo culturing stem cells of different tissue origins are well known in the art of cell culturing. To this effect, see for example, the text book "Culture of Animal Cells—A Manual of Basic Technique" by Freshney, Wiley-Liss, N.Y. (1994), Third Edition, the teachings of which are hereby incorporated by reference. Specific methods of culturing stem cells under conditions which allow cell expansion with no differentiation are known in the art—see for example U.S. Pat. Appl. No. 20050181504, 20050265980, 20050276793 and 20050124003, all of which are incorporated herein by reference. It will be appreciated that the expansion of the stem cells may also be effected during the selection procedure of the present invention and/or following the selection procedure of the present invention.

As mentioned, the selection method of the present invention is based on the observation that stem cells show a higher resistance to pro-apoptotic agents than non-stem cells. Accordingly, a population of cells may be enriched for stem cells by contact with a pro-apoptotic agent under conditions that kill the non-stem cells.

As used herein, the phrase "pro-apoptotic agent" refers to an agent (e.g. chemical or polypeptide) capable of promoting programmed cell death.

Exemplary pro-apoptotic agents that may be used in accordance with the present invention include, but are not limited to TNF-α, FasL, Trail (Apo2 ligand) and Tweak (Apo3 ligand). Such pro-apoptotic agents may be recombinant polypeptides, biochemically synthesized or purified from cell extracts. Recombinant TNF-α, FasL, Trail and Tweak are all commercially available from Companies such as R&D Systems (Minneapolis, Minn.) and Abnova Corporation (Taiwan). Those skilled in the art are aware that many pharmaceutical agents exist that enhance apoptosis. Among such agents are bis-indolylmaleimide-8 and quabain. If desired, these agents may be used in conjunction with the proapoptotic agents of this invention.

According to a preferred embodiment of this aspect of the present invention, the pro-apoptotic agent used to select for stem cells is FasL.

As used herein, the term FasL refers to at least an active portion of a FasL polypeptide capable of binding the Fas receptor and inducing apoptosis. Preferably the FasL is mammalian, for example human. An exemplary polypeptide sequence of human FasL is set forth in GenBank AAC50124. Thus, according to this aspect of the present invention, the FasL may be a biologically active peptide derivative of the Fas ligand polypeptide, a biologically active peptoid derived from Fas ligand polypeptide, or a small organic molecule agonist of Fas ligand activity. The Fas ligand polypeptide can be a biologically active Fas ligand polypeptide such as a Fas ligand polypeptide variant, a Fas ligand polypeptide derivative, a modified Fas ligand polypeptide, or a truncated Fas ligand polypeptide.

According to one embodiment of this aspect of the present invention, the FasL is conjugated to a surface (e.g. cell membrane) such that it is capable of trimerizing the Fas receptor thereby enhancing the efficiency of activation thereof. The FasL may be situated on other surfaces such as for example liposomes or may be linked to biotinylated beads using streptavidin conjugated FasL.

The FasL may be cleavable or non-cleavable from the surface, although according to a presently preferred embodiment of the present invention, the FasL is non-cleavable such that trimerization of the Fas receptor may be maintained. An example of a naturally occurring non-cleaved human Fas ligand expressed only in membrane bound form is set forth in Gen Bank No. AAG60017.1. U.S. Pat. No. 6,951,919 teaches Fas ligands with enhanced apoptotic activities by virtue of being less susceptible to proteolysis.

According to another embodiment of this aspect of the present invention, the FasL is a free polypeptide (i.e. not conjugated to a surface) but is present in a tetrameric state (i.e. non-soluble) such that is capable of inducing trimerization of the Fas receptor and thereby inducing apoptosis. Examples of such polypeptides are known in the art—see for example Pat. Appl. No. 20040018170, incorporated herein by reference. In addition, it has been shown that streptavidin linked FasL is capable of generating tetramers and therefore acting as a pro-apoptotic ligand.

It will be appreciated that the pro-apoptotic agent of the present invention may be conjugated to a dye that is actively excluded from stem cells, such as Hoechst or the like. Such dyes are widely commercially available—e.g. Invitrogen, Molecular Probes. In this way, the stem cells of the present invention may be protected by any negative effects of the pro-apoptotic agents.

Pro-apoptotic agents of the present invention may be contacted with the heterogeneous population of cells for a sufficient time to induce apoptosis of the non-stem cells. Typically, the time taken to initiate apoptosis is about 1 hour, although preferably about 12-18 hours is waited following the onset of apoptosis before the selection procedure is performed. The most effective concentration of FasL for inducing apoptosis of non-stem cells may be determined using in vitro assays and may be dependent on the exact formulation of FasL and the types of cells present in the heterogeneous population.

Alternatively, the pro-apoptotic polypeptides of the present invention may be expressed in the heterogeneous population of the present invention.

Thus, the invention further provides expression constructs encoding a pro-apoptotic polypeptide, which can be used to express same in the heterogeneous cell population of the present invention. For example, a polynucleotide sequence derived from the cloning of mammalian FasL proteins, encoding all or a selected portion of the full-length protein, can be used to generate a recombinant form of a FasL polypeptide. An example of a nucleic acid sequence encoding wild type human FasL is set forth in GenBank No. U1182.1. An example of a nucleic acid sequence encoding naturally occurring non-cleaved human Fas ligand expressed only in membrane bound form is set forth in GenBank No. AF288573.

The nucleic acid construct (also referred to herein as an "expression vector") of the present invention typically includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of the pro-apoptotic polypeptide mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples of mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV50 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Ye t al., (Arch Virol. 2004; 149:51-60).

Recombinant viral vectors are useful for in vivo expression of pro-apoptotic polypeptides since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 1986; 4:504-512] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

The present invention also contemplates up-regulating the apoptotic receptors (e.g. Fas receptor, TNF-α receptor, Tweak receptor and Trail receptor) on the heterogeneous population of cells prior to the selection procedure of the present invention. In this way, the response to the apoptotic signal may be magnified—in a positive direction in the stem cells of the present invention and in a negative direction in the non-stem cells of the present invention.

Methods of up-regulating apoptotic receptors are known in the art such as contacting cells with Interferon γ or TNF-α. Such agents are commercially available from Companies such as Sigma Aldrich and Promokine. Preferably the cells are contacted with these agents for any time between 3 hours to 5 days. Thus, an exemplary method of stem cell selection may comprise incubation of the heterogeneous population of cells with TNF-α for 2 days in order to up-regulate Fas and a subsequent 1 day incubation with Fas-L to kill the non-stem cells. A further example of stem cell selection according to this aspect of the present invention may comprise incubation of the heterogeneous population of cells with Interferon γ for 3 days in order to up-regulate TNF-α receptors and a subsequent 1 day incubation with TNF-α to kill the non stem cells.

It will be appreciated that the resistance of the stem cells of the present invention to apoptotic signals may be enhanced prior to the contacting with the pro-apoptotic agent. For example a dominant negative component of the Fas pathway such as a dominant negative mutant form of the Fas associated death domain (FADD) (e.g. truncated FADD—see e.g. Wu et al. Cell Immunol 2001; 208:137-47) or another molecule capable of blocking the Fas pathway, such as the Fas-associated death domain-like interleukin-1beta-converting enzyme-inhibitory protein (FLIP), may be introduced into the FasL armed cells of the invention to protect the armed cell from FasL-induced death. For further examples on how to increase the resistance of the stem cells to pro-apoptotic agents see Civin et al [U.S. Appl. No. 20040131599].

The ex-vivo stem cells selected according to the method of the present invention can be applied in several clinical situations. The following lists a few.

Cell transplantation: Transplantation of hematopoietic cells has become the treatment of choice for a variety of inherited or malignant diseases. While early transplantation procedures utilized the entire bone marrow (BM) population, recently, more defined populations, enriched for stem cells (CD34+ cells) have been used. In addition to the marrow, such cells could be derived from other sources such as bone marrow stem cells mobilized to the peripheral blood (PB) and neonatal umbilical cord blood (CB). Compared to BM, transplantation with PB cells shortens the period of pancytopenia and reduces the risks of infection and bleeding.

The donor and the recipient can be a single individual or different individuals, for example, autologous or allogeneic transplants, respectively. When allogeneic transplantation is practiced, regimes for reducing implant rejection and/or graft vs. host disease, as well know in the art, should be undertaken. Such regimes are currently practiced in human therapy. The cell populations selected according to the method of the present invention provide a significant depletion of T lymphocytes, which may be useful in the allogeneic and haploidentical transplants setting for reducing graft-versus-host disease.

Most advanced regimes are disclosed in publications by Slavin S. et al., e.g., J Clin Immunol 2002; 22:64, and J Hematother Stem Cell Res 2002; 11:265, Gur H. et al. Blood 2002; 99:4174, and Martelli M F et al, Semin Hematol 2002; 39:48, which are incorporated herein by reference.

In the case of autologous transplantation of recipients with malignancies, contaminating tumor cells in autologous infusion often contribute to the recurrence of the disease. Selecting and expanding non-malignant stem cells will reduce the load of tumor cells in the final transplant.

Prenatal diagnosis of genetic defects in scarce cells: Prenatal diagnosis involves the collection of embryonic cells from a pregnant woman, in utero, and analysis thereof for genetic defects. A preferred, non-invasive, means of collecting embryonic cells involves separation of embryonic nucleated red blood cell precursors that have infiltrated into peripheral maternal circulation. However, since the quantities of these cells are quite scarce, a further application of the present invention would be selection of such cells according to methods described herein, prior to analysis. The present invention, therefore, offers a means to select embryonic stem cells for applications in prenatal diagnosis.

Gene therapy: For successful long-term gene therapy, a high frequency of genetically modified stem cells with transgenes stably integrated within their genome, is an obligatory requirement. In BM tissue, while the majority of cells are cycling progenitors and precursors, stem cells constitute only a small fraction of the cell population and most of them are in a quiescent, non-cycling state. Viral-based (e.g., retroviral) vectors require active cell division for integration of the transgene into the host genome. Therefore, gene transfer into fresh BM stem cells is highly inefficient. The ability to expand and purify a population of stem cells and to regulate their cell division ex-vivo would provide for an increased probability of their genetic modification.

Accordingly, the selected cells of the present invention can be modified to express a gene product as described herein above.

As used herein, the phrase "gene product" refers to proteins, peptides and functional RNA molecules (i.e. polynucleotides). Generally, the gene product encoded by the nucleic acid molecule is the desired gene product to be supplied to a subject. Examples of such gene products include proteins, peptides, glycoproteins and lipoproteins normally produced by an organ of the recipient subject. For example, gene products which may be supplied by way of gene replacement to defective organs in the pancreas include insulin, amylase, protease, lipase, trypsinogen, chymotrypsinogen, carboxypeptidase, ribonuclease, deoxyribonuclease, triaclyglycerol lipase, phospholipase $A_2$, elastase, and amylase; gene products normally produced by the liver include blood clotting factors such as blood clotting Factor VIII and Factor IX, UDP glucuronyl transferae, ornithine transcarbanoylase, and cytochrome p450 enzymes, and adenosine deaminase, for the processing of serum adenosine or the endocytosis of low density lipoproteins; gene products produced by the thymus include serum thymic factor, thymic humoral factor, thymopoietin, and thymosin $α_1$; gene products produced by the digestive tract cells include gastrin, secretin, cholecystokinin, somatostatin, serotinin, and substance P.

Alternatively, the encoded gene product is one, which induces the expression of the desired gene product by the cell (e.g., the introduced genetic material encodes a transcription factor, which induces the transcription of the gene product to be supplied to the subject).

In still another embodiment, the recombinant gene can provide a heterologous protein, e.g., not native to the cell in which it is expressed. For instance, various human MHC components can be provided to non-human cells to support engraftment in a human recipient. Alternatively, the transgene is one, which inhibits the expression or action of a donor MHC gene product normally expressed in the micro-organ explant.

Ex-vivo Selection of Non-Hematopoietic Stem and Progenitor Cells:

Additional applications of the technology proposed herein include the possibility for ex-vivo selection of non-hematopoietic stem and progenitor cells, including, for example, neural stem cells, oligodendrocyte progenitors, and the like. Such stem cells may be forced to differentiate ex vivo along a particular pathway by transfecting the cells such that they express gene products (either polypeptide or polynucleotide products). Alternatively or additionally, the selected cells may be induced to differentiate by culturing in the appropriate medium.

Myelin disorders form an important group of human neurological diseases that are, as yet, incurable. Progress in animal models, particularly in transplanting cells of the oligodendrocyte lineage, has resulted in significant focal remyelination and physiological evidence of restoration of function. Future therapies could involve both transplantation and promotion of endogenous repair, and the two approaches could be combined with ex-vivo manipulation of donor tissue.

U.S. Pat. No. 5,486,359 illustrates that isolated human mesenchymal stem cells can differentiate into more than one tissue type (e.g. bone, cartilage, muscle, or marrow stroma) and provides a method for isolating, purifying, and expanding human mesenchymal stem cells in culture.

U.S. Pat. No. 5,736,396 provides methods for in-vitro or ex-vivo lineage-directed induction of isolated, culture-expanded human mesenchymal stem cells comprising mesenchymal stem cell contact with a bioactive factor effective in inducing stem cell differentiation into a lineage of choice. Further disclosed is a method including introducing culture-expanded lineage-induced mesenchymal stem cells into the original, autologous host, for purposes of mesenchymal tissue regeneration or repair.

U.S. Pat. No. 4,642,120 provides compositions for repairing defects in cartilage and bones. These are provided in gel form either as such, or embedded in natural or artificial bones. The gel comprises certain types of cells. Cells may be committed embryonal chondrocytes or any mesenchymal-origin cells which potentially can be converted to become functional cartilage cells, typically by the inclusion of chondrogenic inducing factors, in combination with fibrinogen, antiprotease and thrombin.

U.S. Pat. No. 5,654,186 illustrates that blood-borne mesenchymal cells proliferate in culture, and in-vivo, as demonstrated in animal models, and are capable of migrating into wound sites from the blood to form skin.

U.S. Pat. No. 5,716,411 reveals a method of skin regeneration of a wound or burn in an animal or human. This method comprises the steps of initially covering the wound with a collagen glycosaminoglycan (GC) matrix, facilitating mesenchymal cell and blood vessel infiltration from healthy underlying tissue within the grafted GC matrix. Subsequently a cultured epithelial autograft sheet grown from epidermal cells taken from the animal or human at a wound-free site is applied on the body surface. The resulting graft has excellent inclusion rates and has the appearance, growth, maturation and differentiation of normal skin.

U.S. Pat. No. 5,716,616 provides methods for treating recipients suffering from diseases, disorders or conditions characterized by bone, cartilage, or lung defects. The methods comprise intravenous administration of stromal cells isolated from normal, syngeneic individuals, or intravenous administration of stromal cells isolated from the recipient subsequent to correction of the genetic defect in the isolated cells. Methods of introducing genes into a recipient individual are also disclosed. The methods comprise obtaining a bone marrow sample from either the recipient individual or a matched syngeneic donor and isolating adherent cells from the sample. Once isolated, donor adherent cells are transfected with a gene and administered to a recipient individual intravenously. Compositions comprising isolated stromal cells that include exogenous genes operably linked to regulatory sequences are disclosed, as well.

In each of the above examples, non-hematopoietic stem and progenitor cells are used as an external source of cells for replenishing missing or damaged cells of an organ. Such use requires purified compositions of stem and progenitor cells for successful application of the proposed therapies. Because of this pressing need for large numbers of purified stem and progenitor cell populations, the methods and applications of the present invention address a critical niche in any of the methods disclosed in the above U.S. patents.

Additional Examples for Both ex-vivo and in-vivo Applications:

Additional applications of stem and progenitor cell expansion include skin regeneration, hepatic regeneration, muscle regeneration and stimulation of bone growth for applications in osteoporosis.

It is expected that during the life of this patent many relevant pro-apoptotic agents will be developed and the scope of the term apoptosis inducing agent is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Animal preparation and transplantation: Mice used in this study were C57Bl/6J (B6, H2$^b$, CD45.2), B6.SJL-PtprC$^a$ Pepc$^b$/BoyJ (H2K$^b$, CD45.1), B6.MRL-Faslpr/J (lpr, H2K$^b$, CD45.2), B6Smn.C3-Tnfsf6gld/J (gld, H2k$^b$, CD45.2) and C57BL/6-TgN(ACTbEGFP)1Osb (GFP, H2k$^b$), purchased from Jackson Laboratories. The mice were housed in a barrier facility. Recipients were conditioned by sublethal (850 rad) and lethal (950 rad) total body irradiation using an X-ray irradiator (RadSource 2000) at a rate of 106 rad/min. The mice were routinely conditioned 18-24 hours prior to transplantation. Notably, X-ray irradiation is different from γ-irradiation in myeloablative dose and toxicity. For transplantation, cells suspended in 0.2 ml phosphate buffered saline (PBS) were infused into the lateral tail vein.

Cell isolation, characterization and staining: Whole bone marrow cells (wBMC) were harvested from femurs and tibia in phosphate buffered saline (PBS, Beit Haemek) in aseptic conditions. For immunomagnetic separation of lineage-negative (lin$^-$) BMC, cells were incubated for 45 minutes at 4° C. with saturating amounts of rat anti-mouse monoclonal antibodies (mAb) specific for CD5, B220, TER-119, Mac-1, Gr-1 and NK1.1. All antibodies were obtained from hybridoma cell cultures, except Ter-119 and NK1.1 (eBioscience). The antibody-coated cells were washed twice with PBS containing 1% fetal calf serum (FCS, Biological Industries) and incubated with sheep-anti-rat IgG conjugated to M-450 magnetic beads at a ratio of 4 beads per cell (Dynal). The unconjugated lin$^-$ BMC were collected by exposure to a magnetic field, and the efficiency of separation was reassessed by flow cytometry using a cocktail of fluorescein-isothyocyanate (FITC)-labeled mAb against the lineage markers (eBioscience and BD Pharmingen). To achieve a higher degree of purity (>95%) the immunomagnetic separation was repeated in some cases.

Long-term (LTR) and short-term (STR) hematopoietic reconstituting cells were isolated by counterflow centrifugal elutriation using a J-6 rotor of a Beckman centrifuge. wBMC harvested from femurs and tibia were fractionated at flow rates of 15, 25 (Fr25), 29 and 33 ml/min at 3000 rpm, and with the rotor off (STR). Fr25 cells were lineage-depleted by incubation at 4° C. with rat-anti mouse mAb against AA-4, CD5, GR-1, Mac-1, B220 (from hybridoma cell lines) and purified TER119 (eBioscience) to obtain the LTR population. The efficiency of lineage-depletion of the LTR cells was reassessed by flow cytometry using a cocktail of fluorochrome-labeled mAb (BD Pharmingen, eBioscience).

For staining with an intracellular dye, the cells were incubated for 20 minutes with 2.5 μM of 5-(and-6-)-carboxyfluorescein diacetate succinimidyl ester (CFSE, Molecular Probes), washed and resuspended.

Apoptotic challenge using FasL protein: The streptavidin-FasL chimeric protein was previously shown to transduce potent apoptotic signals to Fas$^+$ cells [Yolcu E S, et al. Immunity 2002; 17:795-808]. Cells were incubated (5×10$^6$ cells/ml) for 24 hours in α-MEM culture medium supplemented with StemPro Nutrient Supplement (Stem Cell Technologies), 2 mM L-glutamine, 50 μM 2β-ME. In some cases the medium was supplemented with 10 ng/ml stem cell factor (SCF) and 100 ng/ml thrombopoietin (TPO). All supplements were purchased from PeproTech. The cells were challenged by addition of 75-250 ng/ml streptavidin-FasL chimeric protein for 18-24 hours, followed by flow cytometric analysis of apoptosis and death.

Organ harvesting: Spleen, lung and liver were harvested after intracardiac perfusion of 30 ml cold PBS containing 100 units Heparin. The tissues were sectioned into pieces and processed: the lung was digested in 380 u/ml collagenase type V (Sigma) for 60 min at 37° C., the liver was digested in 1500 u/ml collagenase for 20 min at 37° C. All tissues, including spleen, were filtered over a 40 μm mesh, and cell suspensions were washed twice with PBS.

Adsorption of FasL protein on the surface of cells: Cells were suspended in 5 μM freshly prepared EZ-Link Sulfo-NHS-LC-Biotin (Pierce) in PBS for 30 minutes at room temperature. After two washes with PBS the cells were incubated with streptavidin-FasL chimeric protein (100 ng protein/10$^6$ cells) in PBS. The efficiency of adsorption was evaluated by flow cytometry using primary goat anti-streptavidin mAb (Zymed) counterstained with secondary porcine anti-goat IgG (R&D Systems), and anti-FasL antibodies (clone MFL-4, BD Pharmingen). Positive staining was determined on a log scale, normalized with control cells stained with isotype control antibodies.

Flow cytometry: Measurements were performed with a Vantage SE flow cytometer (Becton Dickinson). Nucleated peripheral blood and bone marrow cells were isolated by centrifugation over a ficoll gradient according to the manufacturer's instructions (Cedarlane). Cells were washed in PBS, incubated for 45 min at 4° C. with labeled primary mAb or counterstained with a fluorochrome-labeled secondary mAb. Donor chimerism in syngeneic transplants was determined from the percentage of donor and host peripheral blood lymphocytes (PBL) using monoclonal antibodies against minor antigens CD45.1 (clone A20, eBioscience) and CD45.2 (clone 104, eBioscience).

Cell death and apoptosis was determined in cells incubated with 5 μg/ml 7-aminoactinomycin-D (7-AAD, Sigma) and Annexin-V (IQ products, Groningen, The Netherlands).

The receptors and ligands were identified with a primary labeled mAb: Fas (CD95) clone 15A7 (eBioscience), TNF-R1 (CD120a) clone HM104 (Serotec), TNF-R2 (CD120b) clone TR75-89 (Serotec), Trail-R2 (DR5) clone MD5-1 (eBioscience) and FasL clone MFL4 (BD Pharmingen).

Cell surface markers of putative stem cells were identified as Sca-1 (Ly-6A) clone D7 (eBioscience) and c-kit (CD117) clone 2B8 (eBioscience). Biotinylated antibodies were counterstained with streptavidin conjugated to FITC, phycoerythrin (PE), allophycocyanin (APC) and peridinin chlorophyll a-protein (PerCP, BD Pharmingen).

Semi-quantitative RT-PCR. Total RNA was extracted from the cells using either EZ-RNA II extraction reagent or RNeasy mini columns (Qiagen, Hilden, Germany). RNA was used in the Reverse Transcription reaction along with $pd(T)_{12-18}$ primers. The PCR step was performed using the following set of primer pairs: mouse FAS-Forward 5' GCCTTGGTTGT-TGACCA (SEQ ID NO: 1), Reverse 5' GTACCAGCACAG-GAGCA (SEQ ID NO: 2), generating a 300 bp fragment; mouse FAS-ligand-Forward 5' ACCGCCATCACAACCA (SEQ ID NO: 3), Reverse 5' TCAACCTCTTCTCCTCCA (SEQ ID NO: 4), generating a 500 bp fragment. Primers for β-actin were used as an internal control and normalization of expression.

Colony forming unit (CFU) assay in vitro. $3\times10^4$ cells were plated in 1.2% methylcellulose containing 20% FBS, 1% BSA, 0.1 mM 2β-ME, 10 u/ml recombinant human erythropoietin (EPO), 20 ng/ml recombinant mouse (rm) SCF, 10 ng/ml rm interleukin-3 (IL-3) and 10 ng/ml rmGM-CSF (PeproTech), in Iscove Modified Dulbecco Medium (IMDM). Colonies exceeding 50 cells (CFU-C) were counted after 7-10 days. Streptavidin-FasL chimeric protein was added at incremental concentrations in the range of 200-1,500 ng/ml, or was adsorbed on the surface of the cells via biotinylation [Yolcu E S, et al. Immunity 2002; 17:795-808; Askenasy N, et al. Circulation 2003; 107:1525-1531; Pearl-Yafe M et al., Stem Cells 2007; in press]. Recombinant human soluble FasL (SuperFasL, Alexis) was supplemented at a concentration of 5 ng/ml. Caspases 3 and 8 were inhibited by the addition of Z-DEVD-fmk and Z-IETD-fmk (R&D Systems), respectively.

Statistical analysis. Data are presented as means±standard deviations for each experimental protocol. Results in each experimental group were evaluated for reproducibility by linear regression of duplicate measurements. Differences between the experimental protocols were estimated with a post hoc Scheffe t-test and significance was considered at $p<0.05$.

Example 1

Physiological Fas Activation in Hematopoietic Cell Engraftment

Results

The detrimental consequences attributed to the Fas/FasL interaction in hematopoietic cells would suggest a negative impact in the context of hematopoietic stem and progenitor cell (HSPC) transplants. Suppressive activity of this interaction would suggest that Fas-defective HSPC have an engraftment advantage due to insensitivity to Fas-mediated regulation and/or suppression of donor cell activity. To test this possibility, the present inventors used Fas-defective (lpr) and FasL-defective (gld) mice in syngeneic transplants, to circumvent the immunogenic mechanisms involved in graft rejection and graft versus host disease (GVHD), and to isolate the role of this molecular pair in the early engraftment process. Transplantation of $10^6$ lin⁻ BMC from either wild type (CD45.1) or Fas-defective (lpr, CD45.2) donors into myeloablated (950 rad) syngeneic GFP recipients (CD45.2) resulted in full donor chimerism in the peripheral blood at 3 weeks post-transplantation (n=5). A competitive engraftment experiment was performed by transplantation of $5\times10^5$ lin⁻ BMC from both wild type (wt) and lpr donors into myeloablated syngeneic GFP recipients (n=16). Under these conditions, the chimeras presented 59±5% CD45.1 and 35±4% lpr chimerism at 3 weeks (FIG. 1A), a difference that was sustained at 14 weeks post-transplantation. These data suggest a positive role for the Fas/FasL interaction in the early stages of hematopoietic cell engraftment, with no evidence of Fas-mediated suppression of donor cell activity. On the contrary, the deficient engraftment suggests a supporting role for donor cell Fas.

Figure 1C:
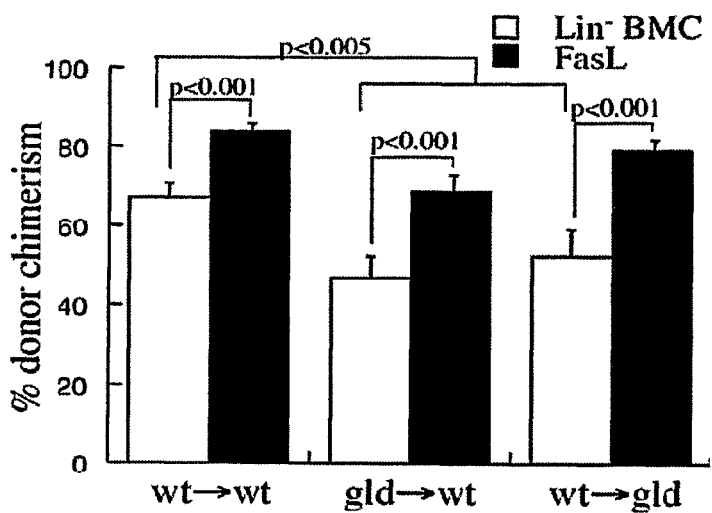
Figure 1D:
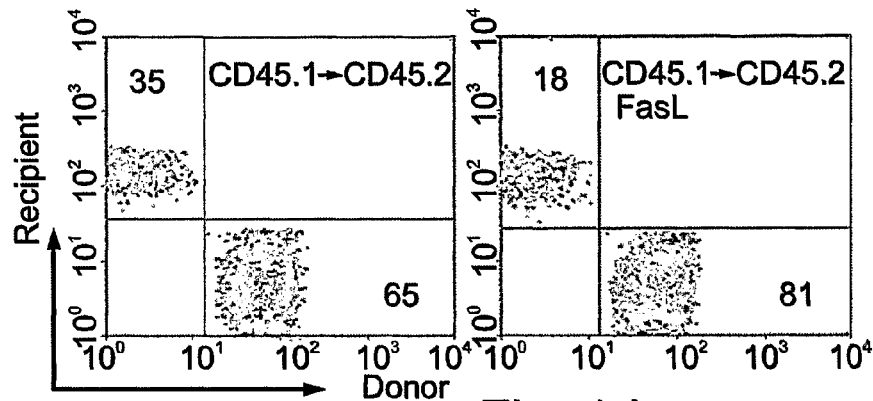

Engraftment was further assayed in syngeneic transplants of $5\times10^5$ lin⁻ BMC into sublethally irradiated (850 rad) recipients, to attain mixed chimerism (FIG. 1B). The first general observation was the deficient engraftment of lpr cells in wt recipients, and reciprocally of wt cells in lpr hosts ($p<0.05$). Interestingly, engraftment was deficient not only when donor cells were Fas-defective (lpr), but also when wt cells were infused into lpr recipients (FIG. 1B), suggesting that more than one mechanism involves Fas/FasL interaction. Furthermore, engraftment was deficient when gld cells were infused into wt recipients, and wt cells into gld recipients (FIG. 1C). The integrated interpretation of these data point to a 20-25% deficient engraftment of cells lacking the Fas receptor and ligand.

Example 2

Transient Display of Ectopic FasL Protein Improves Syngeneic Cell Engraftment

Results

To determine whether the engraftment deficit of gld cells would be restored by FasL, the donor cells were coated with a FasL protein via biotinylation. Expression of FasL protein on the surface of donor gld cells restored their engraftment deficit ($p<0.001$) in syngeneic wt recipients (FIG. 1C). A similar effect was observed when FasL-expressing wt cells were transplanted into gld recipients ($p<0.001$), suggesting donor FasL-host Fas interaction and apparent autocrine Fas/FasL activity in the engrafting cells. Modulation of engraftment was attributed to specific effects of FasL, and not to secular effects of protein decoration on the surface of cells. Decoration of wt-BMC with FasL protein via biotinylation improved ($p<0.005$) early engraftment in syngeneic wt recipients (FIG. 1D), and the mice proceeded to develop full donor chimerism at 16 weeks post-transplantation. These results suggest that engrafting BMC are insensitive to FasL-induced apoptosis, and that expression of this protein improves short-term engraftment without harming long-term repopulating cells.

Example 3

Figure 1E:
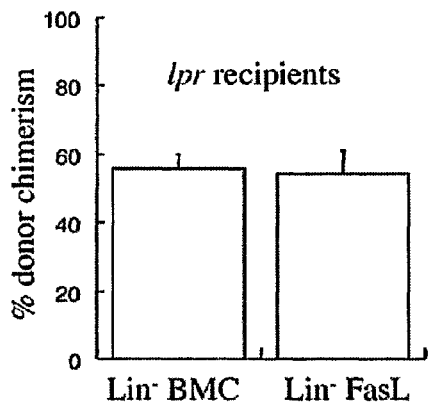

The Primary Target of the Donor Cell FasL is the Marrow Stroma in Syngeneic Transplants Results To ascertain whether the engraftment-facilitating effect of ectopic FasL protein operated through Fas signaling in the host, cells from wild type mice were transplanted into Fas-defective lpr recipients (n=8). The engraftment advantage achieved by expression of the FasL protein on the surface of the cellular allografts was lost, indicating that the mechanism involved a competent Fas signaling pathway in the host (FIG. 1E). These results were further proof that the enhanced engraftment of FasL decorated cells was a specific effect of FasL and not an artifact of ex vivo cell manipulation.

Figure 1F:
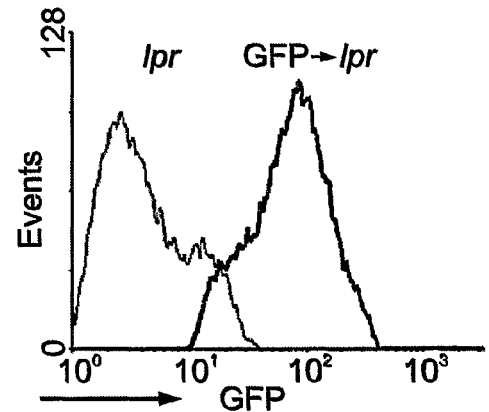
Figure 1G:
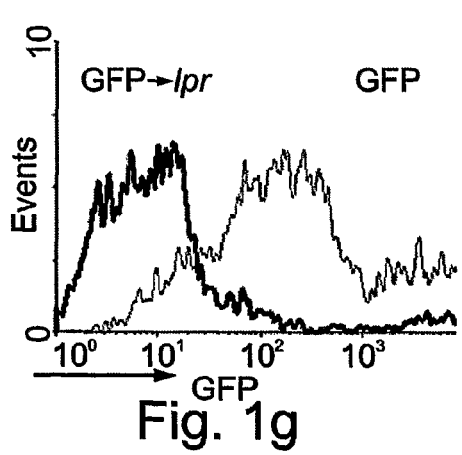
Figure 1H:
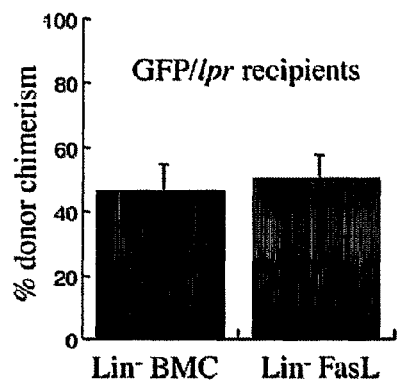

A veto activity of FasL-decorated lin⁻ BMC may operate at the systemic level, where it prevents destruction of pre-homed BMC by the host immune system, or in the bone marrow, where it may remove the residual host cells that survived irradiation. In syngeneic transplants, immune modulation would not be expected to be a relevant variable in the engraftment process. The residual host cells that may be targeted by donor cell-FasL include immunocytes, HSPC and bone marrow stroma. The evidence of a non-immunogenic mechanism involved in the engraftment-supporting effect of FasL led the present inventors to seek the specific cellular targets of FasL decorated cells in the host (stroma or residual host HSPC and immunocytes that survived irradiation). The present inventors generated a chimeric mouse with $Fas^-$ stroma and $Fas^+$ hematopoietic cells by transplantation of $10^7$ whole BMC from GFP donors into myeloablated (950 rad TBI) lpr recipients. At 6 weeks post transplantation these mice displayed full donor hematopoietic chimerism in the peripheral blood and the bone marrow (FIG. 1F). To ascertain that the marrow stroma was of the lpr host phenotype, the marrow aspirate was plated in long-term cultures. The predominant phenotype of the cells that grew in culture was of the lpr host ($GFP^-$) origin, after gating out the $CD11c^+$ and $CD45^+$ cells (FIG. 1G). Sublethally-irradiated (850 rad) chimeras served as recipients of a second transplant of syngeneic CD45.1 cells. The levels of hematopoietic chimerism were similar after transplantation of naïve and FasL-coated $lin^-$ BMC (FIG. 1H), similar to the loss of FasL-mediated engraftment advantage in lpr recipients (FIG. 1E). By elimination, these data indicate that the primary target of donor cell FasL is the mouse stroma, rather than veto activity on residual hematopoietic cells in the host bone marrow.

Example 4

Figure 2A:
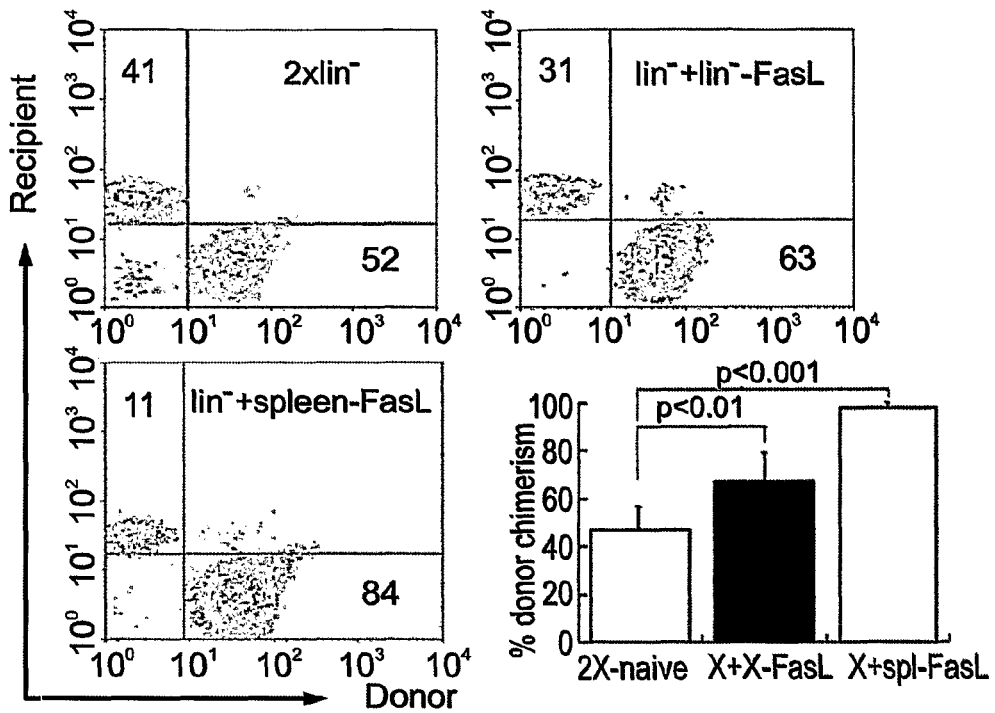
FIGS. 2A-G illustrate that ectopic expression of FasL protein improves allogeneic cell engraftment. A. Radiation-conditioned allogeneic (H2K$^d$→H2K$^b$) recipients (850 rad) were injected with 10$^6$ naïve lin$^-$ BMC in conjunction with 10$^6$ lin$^-$ BMC or splenocytes coated with FasL protein, and a control group transplanted with 2×10$^6$ naïve lin$^-$ BMC (n=5). The levels of donor chimerism determined in the peripheral blood at 3 weeks post transplantation. B. Streptavidin-FasL chimeric protein was efficiently adsorbed on the surface of BMC via biotinylation. The protein was detected with an anti-FasL monoclonal antibody in flow cytometry. C. Expression of ectopic FasL protein improved the engraftment of allogeneic (BALB/c=H2K$^d$) cells transplanted into sublethally irradiated (850 rad) recipients (B6=H2K$^b$). D. Mice transplanted with unmanipulated and FasL-coated lin$^-$ BMC proceeded to develop full chimerism at 16 weeks post-transplantation (n=10). E. At 14 weeks after primary transplantation (H2K$^d$→H2K$^b$) the chimeric mice served as donors of wBMC to secondary sublethally irradiated (H2K$^b$) hosts (n=5). Chimerism was measured in peripheral blood at 14 weeks post-transplantation. F. Splenocytes of B6 mice (H2K$^b$) injected with 8×10$^6$ naïve or FasL-coated allogeneic lin$^-$ BMC (H2K$^d$) were evaluated in a 5-day MLR assay at 7 days post-transplantation (n=6). Splenocytes of B10.BR mice (H$_2$K$^k$) served as third party antigens. G. The spleens of mice injected with 8×10$^6$ naïve or FasL-coated allogeneic splenocytes (H2K$^d$→H2K$^b$) were evaluated in MLR (n=5).

Ectopic Expression of FasL Enhances the Engraftment of Allogeneic Hematopoietic Cells Results To determine the impact of donor cell expression of FasL at the systemic level, the FasL chimeric protein was expressed on the surface of splenocytes and $lin^-$ BMC via biotinylation. These cells were transplanted along with $10^6$ naïve $lin^-$ BMC into irradiated allogeneic hosts ($H2K^d \rightarrow H2K^b$). The levels of engraftment were significantly improved by expression of the FasL protein on $lin^-$ BMC (p<0.001), and were further improved by its expression on donor splenocytes (p<0.001), as compared to a double number of naïve $lin^-$ BMC (FIG. 2A). These data suggest that inhibition of the alloresponses was beneficial to donor hematopoietic cell engraftment. However, it remained unclear whether the engrafted cells were within the naïve or the FasL-coated subsets of $lin^-$ BMC.

Figure 2B:
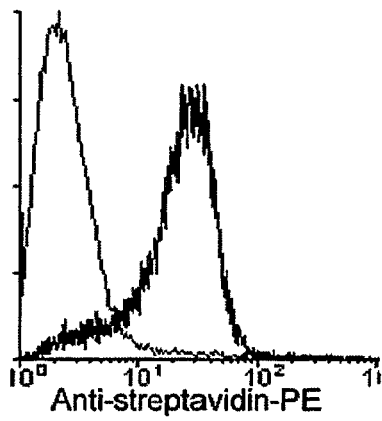
Figure 2C:
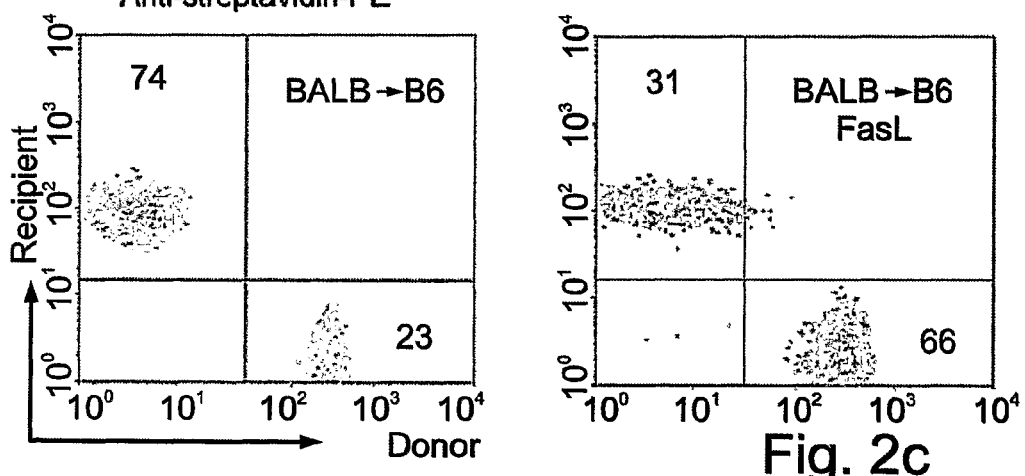
Figure 2D:
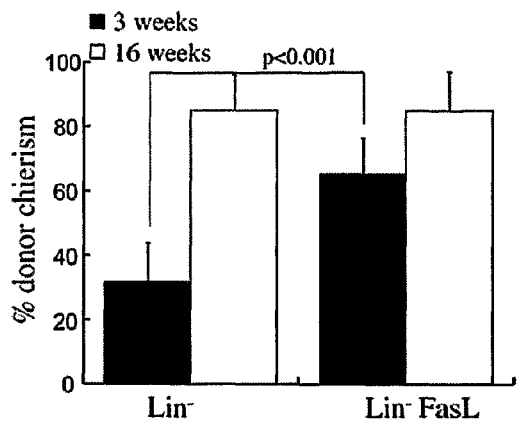
Figure 2E:
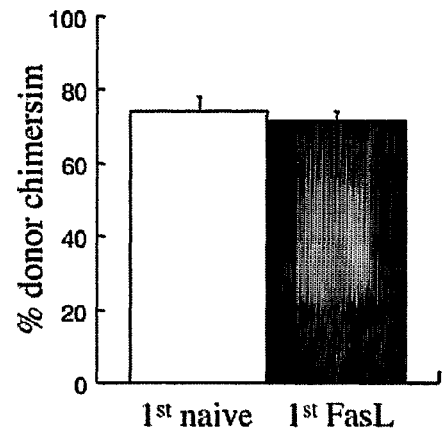

To determine whether expression of FasL on all the grafted $lin^-$ BMC cells would impact engraftment, the protein was adsorbed on the surface of donor cells with almost absolute efficiency (FIG. 2B). Transplantation of $1.5 \times 10^6$ FasL-decorated allogeneic $lin^-$ BMC resulted in superior levels (p<0.001) of donor hematopoietic chimerism at 3 weeks as compared to unmodified cells (FIG. 2C). All mice proceeded to develop full chimerism at 16 weeks post-transplantation, indicating that transient display of the ectopic protein did not influence the eventual establishment of durable hematopoietic chimerism (FIG. 2D). To test whether the improved early engraftment did not cause extinction of the stem cells, sequential transplants were performed. Transplantation of $lin^-$ BMC from the full chimeras into secondary myeloablated hosts showed no significant differences in engraftment (FIG. 2E). Thus, expression of the FasL protein on donor cells was well tolerated, improved their short-term engraftment, and did not impair their long-term hematopoietic reconstituting potential.

Example 5

Expression of FasL Protein Blocks Alloreactivity in a Fas-dependent Manner

Figure 2F:
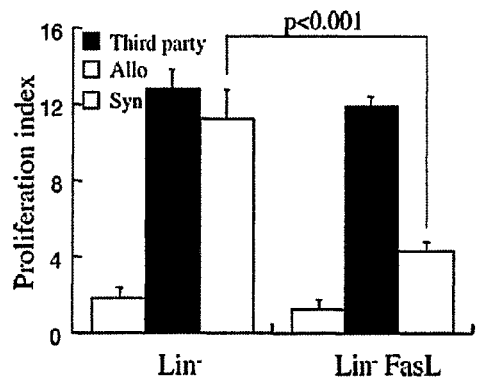
Figure 2G:
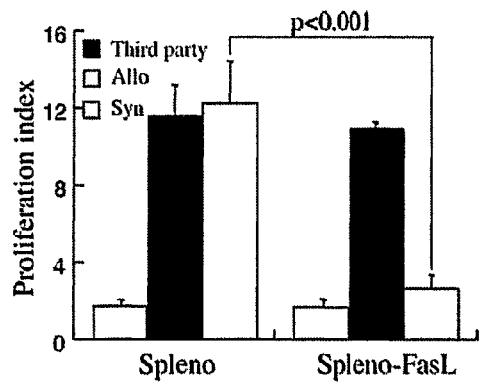

The likely mechanism in support of allogeneic cell engraftment is inhibition of the alloresponses by the overexpressed FasL protein through activation-induced cell death (AICD) of the host immune cells. To provide direct evidence for the immunoinhibitory role of FasL, cells coated with the protein were injected intraperitoneally into allogeneic hosts. The responses of recipient splenocytes were assayed after 7 days in a mixed lymphocyte reaction (MLR). FasL-decorated $lin^-$ BMC and splenocytes specifically blocked alloreactive responses, and the responses to third party antigens remained intact (FIGS. 2F-G). FasL-decorated splenocytes were more effective than $lin^-$ BMC in their inhibition of alloreactive T cell responses. This may be due to the prevalence of professional antigen presenting cells in the spleen, capable of effectively activating alloreactive T cells that become sensitive to FasL-mediated killing through AICD (3,35,36). Taken together, these data demonstrate a very early involvement of FasL in the process of hematopoietic cell engraftment, which is in part mediated by systemic inhibition of the alloimmune responses against the graft. This is consistent with the superior homing of syngeneic versus allogeneic donor cells, which was previously reported by the present inventors (1).

Example 6

Death Receptors are Upregulated in Donor Cells

Results

Figure 3A:
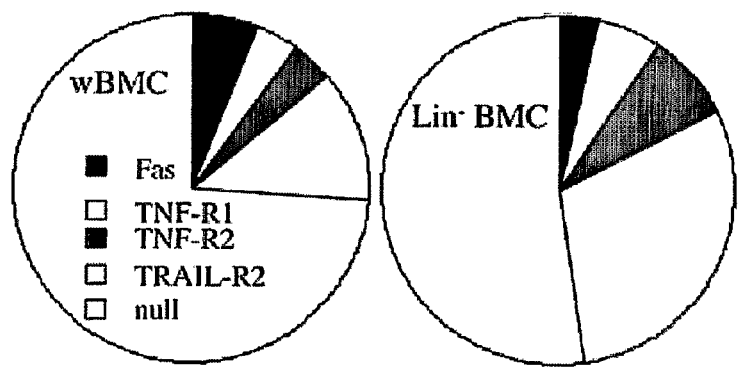
Figure 3B:
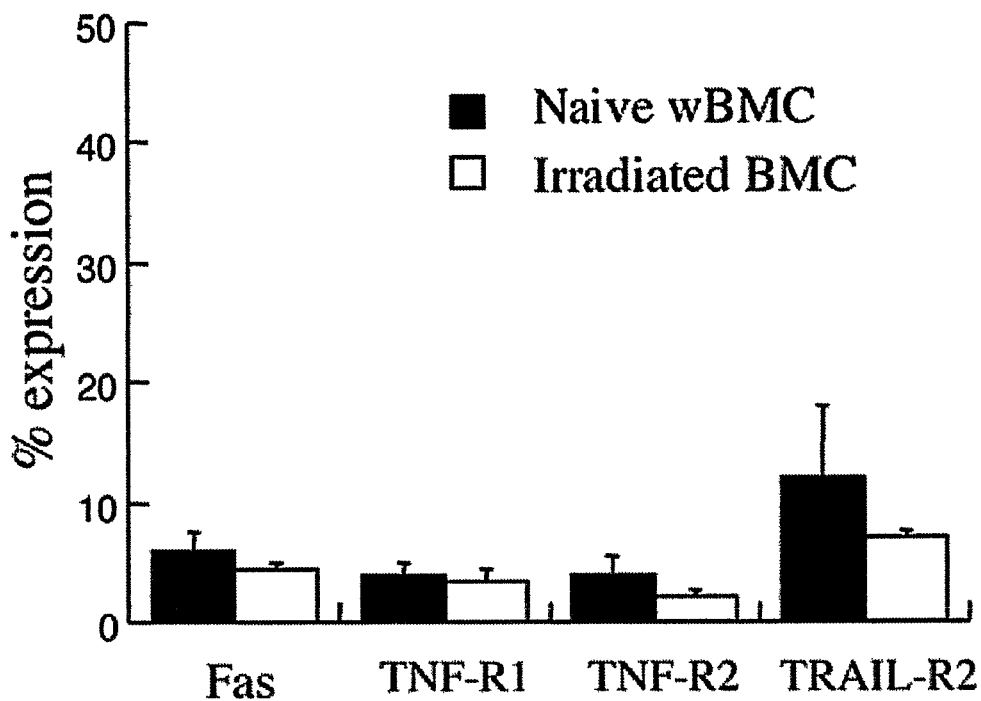

The levels of Fas, TNF and TRAIL receptors were evaluated in naïve nucleated whole BMC (wBMC) and lineage-depleted ($lin^-$) BMC harvested from naïve C57B1/6 and BALB/c mice. The prominent difference was the more accentuated expression of the TNF and TRAIL receptors in the $lin^-$ subset, as compared to wBMC (FIG. 3A). To monitor changes in death receptor expression after transplantation $lin^-$ BMC were used, because in wBMC transplants there is preferential homing of more primitive progenitors as compared to mature cells (1). Following transplantation of $lin^-$ BMC into irradiated (850 rad) syngeneic recipients (CD45.1→CD45.2), the bone marrow was harvested and analyzed by gating on the donor and host cells. The residual host cells that survived irradiation (after 48 hours) showed minor changes in the expression of these receptors as compared to their distribution in naïve BMC (FIG. 3B). The day-2 bone marrow (BM)-homed donor cells displayed a remarkable upregulation of the Fas and both TNF receptors (p<0.001) as opposed to a relatively small increase in the TRAIL-R2 receptor (FIG. 2C). Subsequently, death receptor expression increased to 60-75% of the donor cells after 6 days (FIG. 2D). In parallel, the residual host BMC showed a modest increase in Fas to 14.5±3%, TNF-R2 to 22.5±2.5% and TRAIL 19.5±0.5% at 6 days post-transplantation (p<0.001 vs baseline values). Under these transplant conditions the mice developed ~50% donor chimerism at 3 weeks (n=15) and proceeded to develop full donor chimerism after 16 weeks. Taken together, these data show acute expression of death receptors in donor cells early after transplantation.

Example 7

Dependence of Death Receptor Expression on Cycling and Differentiation

Results

Figure 3C:
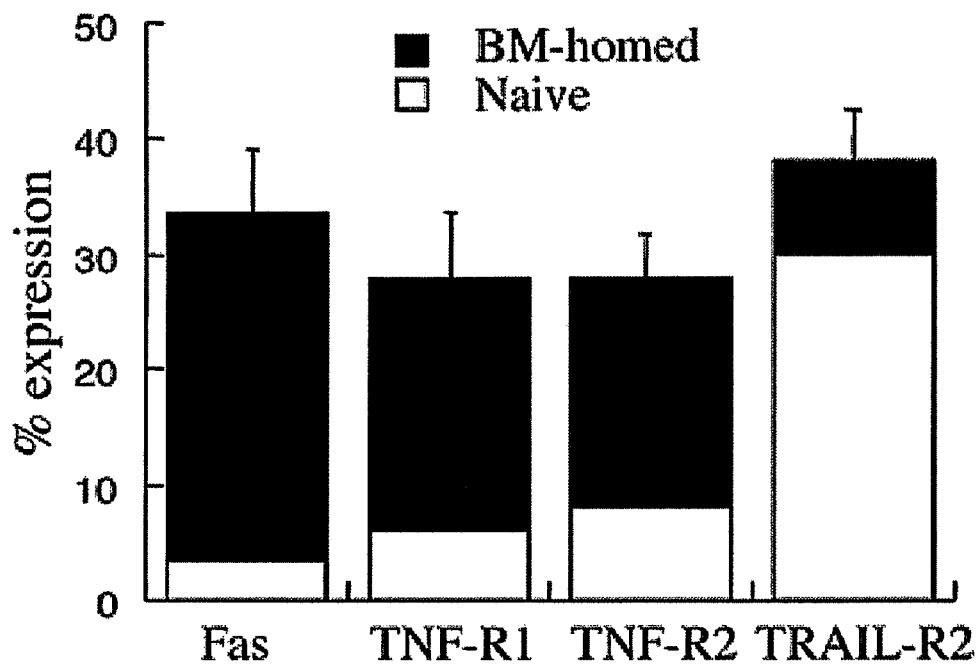
Figure 3G:
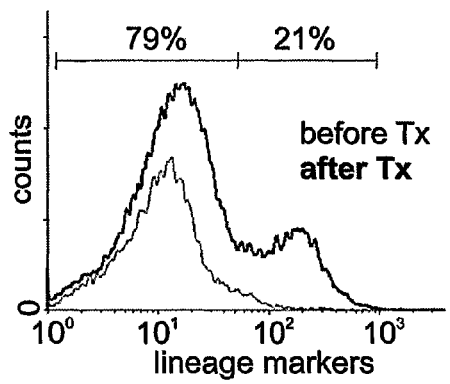
Figure 3H:
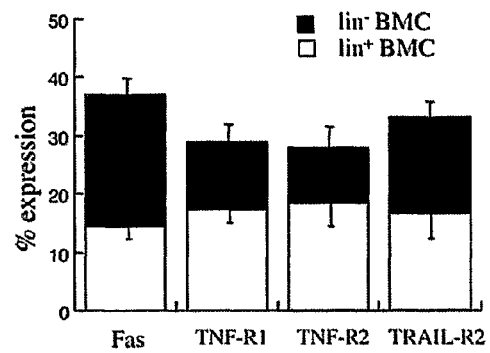

Expression of the death receptors might be induced by division and early differentiation, as some donor cells engage in cycling early upon homing to the bone marrow (1). Therefore, the expression of TNF family receptors was monitored in donor cells during the proximal seeding process in reference to CFSE dilution and expression of lineage markers. Donor cells were pre-labeled with the intracellular dye CFSE prior to transplantation. Approximately one third of the cells displayed significant dilution of CFSE, indicative of cell division after homing to the host bone marrow (FIG. 3E). The receptors were primarily expressed in the $CFSE^{dim}$ fraction of cells (p<0.001) as compared to cells that remained $CFSE^{bright}$ at 24 hours post-transplantation (FIG. 3F). A similar uneven distribution was observed in cells that expressed lineage markers within the first 48 hours post-transplantation (FIG. 3G). The increase in BM-homed $lin^+$ BMC from 5±1.7% to 20±2% within 2 days after transplantation was accompanied by expression of the death receptors (FIG. 3H). These data indicate that expression of the receptors is associated primarily with early cell cycling and differentiation upon homing to and seeding in the host bone marrow.

Example 8

Figure 4A:
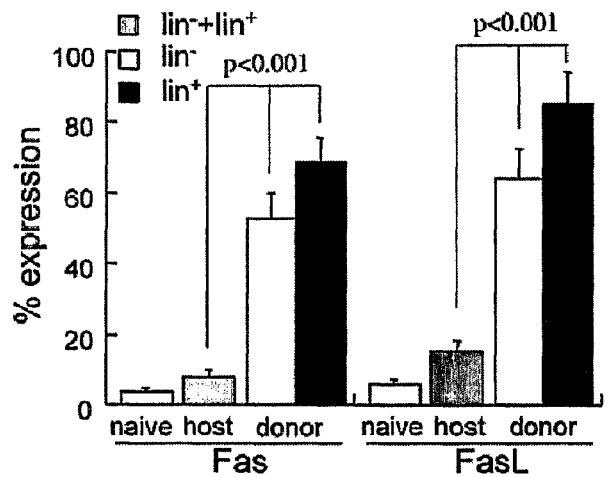
Figure 4B:
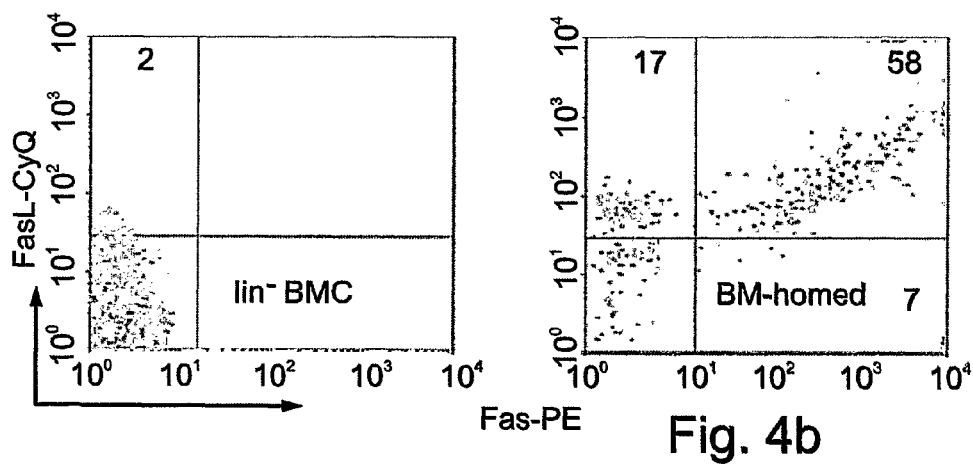

Fas/FasL are Co-expressed by the Donor Cells Upon Transcriptional Activation Results In view of the acute expression of the death receptors, the present inventors attempted to determine whether the cognate ligands are expressed as well. The only membrane-bound ligand in the TNF superfamily is FasL. Two days following transplantation of allogeneic $lin^-$ BMC into irradiated hosts ($H2K^d \rightarrow H2K^b$), the bone marrow-homed cells were harvested and analyzed for the expression of the Fas receptor and ligand. While the residual BMC of the host displayed a moderate up-regulation in the expression of these molecules, the donor cells showed a remarkable up-regulation of Fas and FasL within hours after homing to the bone marrow (FIG. 4A). The constitutive joint expression the Fas receptor and ligand (FIG. 4B) was likely the result of the skewed cytokine environment in the irradiated bone marrow, and upregulation of these molecules by cycling bone marrow cells.

To determine whether the increased expression of Fas and FasL was regulated at the level of RNA transcription, an RT-PCR analysis was performed of the donor cells (prior to transplantation). Nucleated whole bone marrow cells expressed significant levels of mRNA encoding Fas and trace amounts of mRNA encoding FasL (FIG. 4C). mRNA transcripts for both molecules were undetectable in the $lin^-$ BMC used for the transplants. Thus, the appearance of the Fas and FasL proteins on the grafted cells was induced at the transcriptional level.

Example 8

Dynamic Expression of Fas/FasL in Grafted Cells upon Interaction with Different Stroma Results Changes in expression of the Fas receptor and its ligand in hematopoietic cells occur in response to multiple environmental factors and differentiation events (4-14,23). The bone marrow stroma is the only microenvironment that provides a site for definitive engraftment of HSPC. To test whether upregulation of Fas and FasL expression characterized only bone marrow-homed cells, donor cells that homed to the various organs of syngeneic hosts (CD45.1→CD45.2) were analyzed. Both the receptor and its ligand were upregulated in donor cells that homed to the bone marrow (FIG. 4D) and lung (FIG. 4E). In variance, the grafted cells that homed to the spleen (FIG. 4F) and liver (FIG. 4G) primarily up-regulated their FasL expression. These molecules were transiently expressed in donor cells that homed to the lung and liver (to peak levels at 24 hours post-transplantation), whereas they were progressively expressed in bone marrow and spleen-homed cells. In parallel, radiation injury induced the expression of these molecules in the parenchymal cells of these organs (FIG. 4D-G). The concomitant up-regulation in parenchymal and grafted cells in the various organs suggests that the expression of Fas and FasL is partially induced by factors (chemokines and cytokines) released as a result of radiation-injury. Nevertheless, other inductive stimuli of Fas and FasL expression vary in the different organs.

Example 9

Death Receptors are Induced by Conditioning and Interaction with the Marrow Stroma Results To determine extrinsic cellular factors that affect expression, the receptors were monitored after infusion into non-irradiated syngeneic (CD45.1→CD45.2) recipients. Under these conditions the expression of death receptors and FasL was approximately 40-65% lower than the levels in irradiated hosts, indicating that release of chemokines and cytokines after stromal injury was partially responsible for death receptor expression. In subsequent experiments lin– BMC were incubated in femurs ex vivo for 6 hours and the levels of expression were determined by flow cytometry. This brief incubation procedure increased Fas expression from 3.5±1.2% to 11.8±3.2% (p<0.001) and FasL from 6±1.5% to 12.2±2.8% (p<0.005), positively identifying the cell-stroma interaction as an important inductive factor of these molecules.

Example 10

Expression of Death Receptors in Candidate Hematopoietic Stem and Progenitor Cells Results The nature of the cells that upregulated the death receptors were investigated and whether these cells fell in the subsets of progenitors with hematopoietic reconstitution potential. Stem cells account for ~0.5% of whole BMC, thus their incidence in $lin^-$ cells is small, and isolation procedures based on phenotype usually yield subsets of BMC with marked functional heterogeneity. Two isolation procedures were used to enrich for hematopoietic stem cells and progenitors.

A. Phenotypically-characterized Stem and Progenitor Cells

Murine HSPC fall largely within the subset phenotypically defined as $lin^-Sca-1^+c-kit^+$ [37,38]. The distribution of death receptors was measured in subsets of BM-homed donor cells expressing these markers at 2 (n=7) and 6 days (n=5) after transplantation of $CFSE^+lin^-$ donor cells. After 48 hours, the death receptors were primarily expressed in $Sca-1^+$ cells (FIG. 5A) and predominantly in $c-kit^-$ cells (FIG. 5B). While there were no significant changes in the $Sca-1^+$ fraction (11.5±2% of $CFSE^+lin^-$ BM-homed donor cells) and death receptor expression (FIG. 5A), the $c-kit^+$ subset decreased from 32±5% on day 2 to 20±3% on day 6 (FIG. 5B). This reduction in number was accompanied by a relative increase in fraction of c-kit$^+$ cells expressing the receptors (p<0.05 for Fas, TNF-R2 and TRAIL). The decrease in fraction and absolute number of c-kit$^+$ cells negative for the TNF receptors was rather unexpected, as one might expect these receptors to mediate cell apoptosis.

Further analysis of the CFSE$^+$lin$^-$Sca-1$^+$c-kit$^+$ subset of cells, which consist of the most primitive candidate HSPC, revealed expression of all the death receptors at 48 hours post-transplantation (FIG. 5C). An example of TNF-R1 expression is shown in FIG. 5D. Likewise, virtually all CFSE$^+$lin$^-$Sca-1$^+$c-kit$^+$ cells, which best correspond to the repopulating HSPC, were positive for Fas and FasL (FIG. 5E-F). Within the subset of lin$^-$c-kit$^+$ cells, ~30% expressed Fas and ~85% expressed FasL (FIG. 5E). Taken together, these data indicate that the most primitive murine progenitors up-regulate the death receptors soon after transplantation, and maintain this expression over the next days.

B. Expression in Short- and Long-term Hematopoietic Reconstituting Cells

To purify two cell populations with distinctive long-term (LTR) and short-term hematopoietic reconstituting (STR) potential a density-based isolation procedure was used. Small cells collected at an elutriation flow rate of 25 ml/min were processed by lineage depletion to yield a fraction (Fr25 lin$^-$) enriched in LTR cells (FIG. 5G), while the large STR subset was collected at the end of BMC fractionation in the rotor off position. The majority of mice transplanted with Fr25 lin$^-$ cells succumbed (8/11) within the period usually observed in myeloablated mice that did not receive cellular transplants. Mice transplanted with STR cells survived for periods of several weeks and most of them (5/8) failed to establish durable donor-type chimerism. In variance, mice transplanted with both cell populations (LTR+STR) showed durable engraftment and competent hematopoiesis in serial transplants (not shown). These data are consistent with previous reports on the early and late hematopoietic reconstituting potential of these cell subsets.[35]

Analysis of freshly-elutriated cells revealed expression of FasL in 27±4% of the Fr25 lin$^-$ cells (FIG. 5H), and flow cytometric analysis of the contaminating lymphocytes showed expression in the lin$^-$ BMC. This suggests constitutive FasL expression in a fraction enriched in LTR stem cells. Both subsets were next transplanted into irradiated (850 rad) syngeneic recipients (CD45.2→CD45.1) and were harvested after two days for analysis. The bone marrow-homed Fr25 lin$^-$ and STR cells showed marked up-regulation of both Fas and FasL upon homing to the bone marrow, with higher levels of expression (p<0.001) in the STR progenitors (FIG. 5H). Thus, the most primitive subsets of stem cells and progenitors with long-term and short-term hematopoietic reconstituting potential respectively, expressed the death receptors early after homing to the bone marrow.

Example 11

Bone Marrow-homed Cells are Resistant to Fas-mediated Apoptosis

Results

The remarkable up-regulation in Fas receptor expression suggests that the donor cells become sensitive to apoptosis. To test this possibility, radiation-conditioned mice (850 rad) were transplanted with syngeneic lin$^-$ BMC (CD45.1→CD45.2), and the BM-homed cells were harvested from the femoral marrow after 2 days. These cells were exposed to an apoptotic challenge with 250 ng/ml FasL protein for 18 hours in vitro in the absence of supporting chemokines and serum to enhance cell susceptibility to apoptosis. The FasL challenge revealed a remarkable resistance of the bone marrow-resident cells to apoptosis (FIG. 6A). Among the residual host BMC that survived radiation, the resistance to FasL-induced apoptosis was expected due to the low levels of Fas expression. In variance, approximately 45% of the BM-homed donor cells were positive for Fas at 48 hours post-transplantation. Measurements of apoptosis in reference to Fas and lineage marker expression (FIG. 6B) demonstrated that the majority of Fas$^+$ BM-homed donor cells were insensitive to FasL-induced apoptosis.

The same apoptotic challenge was applied to BM-homed cells following transplantation of elutriated LTR and STR subsets (FIG. 6C). Day-2 BM-homed cells showed relative insensitivity to the FasL protein and apoptosis was significantly lower as compared to the naïve elutriated cell subsets (p<0.001). Measurements of apoptotic cell death in reference to Fas expression (FIG. 6D) revealed that Fas$^+$ cells in both LTR and STR subsets were insensitive to FasL-induced apoptosis. The Fas$^+$LTR cells were more resistant to FasL-induced apoptosis as compared to the Fas$^+$STR cells. Similar experiments were performed by submitting the day-2 BM-homed cells to TNF-α and TRAIL, yielding a consistent resistance of the lin$^-$ BMC to apoptosis mediated by the cognate receptors.

Example 12

The Impact of Receptor Cross Talk on Cell Sensitivity to Apoptosis

Prior studies showed induction of the Fas receptor by TNF, to which has been attributed severe detrimental consequences on the viability and function of hematopoietic cells (15-22, 28-30). Early up-regulation of the TNF receptors indicated that ~30% of all donor cells (FIG. 3C) and 89-93% of lin$^-$Sca-1$^+$c-kit$^+$ cells expressed receptors for TNF and FasL after 2 days (FIG. 5C). Therefore, BM-homed cells harvested after 1-2 days and exposed to an apoptotic challenge with FasL protein, were monitored for apoptosis in reference to expression of the TNF superfamily receptors. To increase the general sensitivity to apoptosis, cells were incubated without supplements and chemokines in the medium. There were no significant variations in fractional death within the subsets positive for the receptors, and FasL did not induce apoptosis in cells staining positive for the TNF and Fas receptors (FIG. 6E). These data suggest that inductive cross-talk between the death receptors is not associated with sensitization of a particular subset to FasL-induced apoptosis. This insensitivity could be caused either by lack of receptor co-expression or insensitivity of certain subsets of cells to Fas-mediated apoptosis. In view of the co-expression of all the death receptors by the most primitive HSPC, these data point to insensitivity of the cells to apoptosis rather than lack of receptor to sense the apoptotic trigger.

Example 13

Figure 6G:
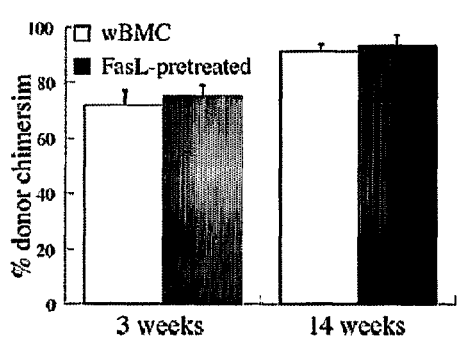

Depletion of Apoptosis-sensitive Cells Does Not Abolish the Hematopoietic Reconstituting Potential of Progenitors and Stem Cells The present inventors next questioned whether the stem and progenitor cells responsible for durable and short term hematopoietic reconstitution of myeloablated mice reside within the apoptosis-sensitive or the apoptosis-resistant subsets of BMC. Cells preincubated in vitro with FasL protein were transplanted into sublethally conditioned (850 rad) syngeneic (CD45.1→CD45.2) recipients (see Example 14, herein below). The levels of chimerism were equivalent at 3 weeks (FIG. 6F), and all recipients proceeded to develop full donor chimerism at 14 weeks post-transplant (FIG. 6G). Bone marrow cells of the chimeras were used as donors to secondary myeloablated (950 rad) recipients (CD45.2). All secondary recipients (n=7) displayed full donor chimerism after 12-16 weeks. Taken together, these data indicate that both the short and long-term hematopoietic reconstituting cells are unaffected by brief exposure to the pro-apoptotic FasL protein. Assuming that the progenitors resided in the lin$^-$ fraction, the same experiment was performed by exposing lin$^-$ BMC to FasL before transplantation. Similar levels of chimerism (n=6) attained after transplantation of lin$^-$ BMC incubated for 24 hours with medium (66±5.8%) and with FasL protein (65±4.1%) provide direct evidence of the insensitivity of progenitors to apoptosis.

Figure 6H:
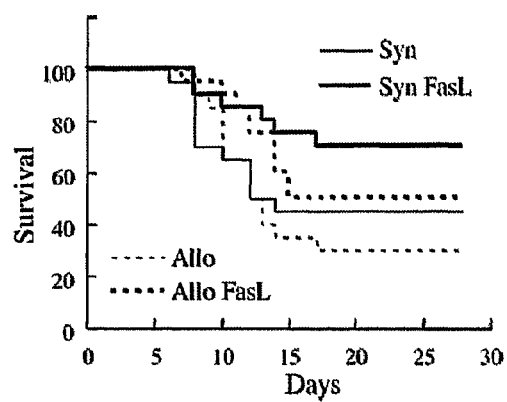

To test whether pre-incubation with proapoptotic ligands improves the outcome of transplants, small numbers of cells were infused. Notably, this incubation period was found to induce Fas expression and induce apoptosis in a fraction of the mature BMC (see Example 14, herein below). The limiting number of lin$^-$ cells required to rescue myeloablated syngeneic hosts (950 rad) is about 2×10$^5$ cells, therefore the mice were infused with 1.5×10$^5$ BMC (FIG. 6H). At 4 weeks after syngeneic transplantation (CD45.2→CD45.1), the survival of recipients of cells preincubated with FasL was superior (14/20) to that of mice transplanted with BMC preincubated in (FasL-free) medium (9/20). Similar differences in survival were observed in the allogeneic transplants (H2K$^b$→H2K$^d$), survival of 10/20 and 6/20 mice transplanted with FasL-pretreated and control BMC, respectively. Thus, pre-incubation with FasL protein improved the radioprotective qualities of the grafted cells. The present inventors next evaluated whether the activation of the hematopoietic progenitors by FasL caused extinction of the stem cells with long-term reconstituting potential. Bone marrow cells of the chimeras were harvested 12 weeks following the first transplants and were infused into secondary myeloablated syngeneic recipients (CD45.1). Transplantation of half of the cellular contents of a femur into each one of the secondary recipients resulted in full donor chimerism after 16 weeks, indicating that stem cell self-renewal was preserved after incubation with the pro-apoptotic ligand.

Example 14

Sensitivity of Naïve Bone Marrow Cells to Apoptosis

Results
The behavior of naïve bone marrow cells in response to apoptotic stimuli in vitro was tested in a series of experiments. Incubation of wBMC for 24 hours with FasL protein resulted in apoptotic death of ~40% of the cells (FIG. 7A), with the major fraction of apoptotic cells being contained in the lin$^+$ subset. Further analysis revealed that all major lineages of BMC were sensitive to Fas-mediated apoptosis (FIG. 7B). Starting from a low incidence of the death receptors (FIG. 3A), the expression of Fas was stimulated in naïve wBMC under these incubation conditions (FIG. 7C). Nevertheless, a significant fraction of the lin$^-$Fas$^+$ cells were insensitive to FasL-mediated apoptosis. Incubation of lin$^-$ BMC in the same conditions confirmed the upregulation of Fas, and further showed that approximately 50% of the lin$^-$Fas$^+$ cells were insensitive to apoptosis (FIG. 7D). Unexpectedly, FasL was more potent in induction of Fas than a combination of 10 ng/ml stem cell factor (SCF) and 100 ng/ml thrombopoietin (TPO).

Figure 7E:
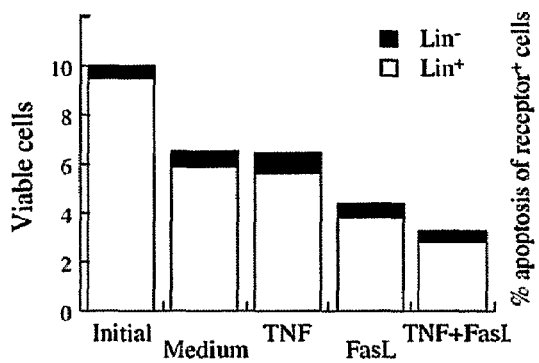
Figure 7F:
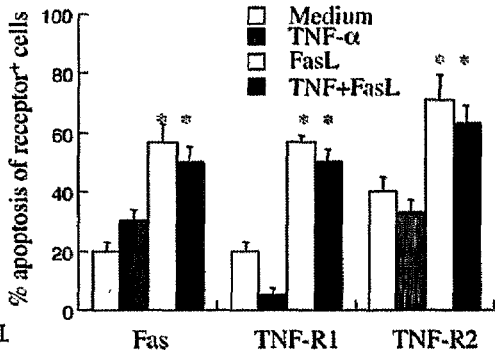

Subsequent incubations were performed for 1, 3 and 5 days and with the addition of SCF+TPO or SCF+TPO+IL-3 as growth factors that support the survival of hematopoietic cells in culture. A series of pilot studies have indicated lack of significant effect of cell pre-incubation with TNF-α as an apoptotic trigger. Furthermore, due to the presumed function of TNF-α in induction of Fas expression and in sensitization to apoptosis, cells were incubated for 3 days with this agent and FasL was added during the last 24 hours of incubation. The absolute number of cells decreased, however the fraction of lin– BMC was largely preserved (FIG. 7E). Apoptosis was analyzed in reference to expression of Fas and TNF receptors (FIG. 7F). Incubation in medium showed higher rates of apoptosis in TNF-R2$^+$ cells as compared to Fas$^+$ and TNF-R1$^+$ cells (p<0.001). The presence of TNF-α in the medium had a small effect on Fas$^+$ and TNF-R2$^+$ cells and decreased apoptosis in TNF-R1$^+$ cells (p<0.001), suggesting that this receptor was involved in cell stimulation rather than inhibition. Exposure to FasL during the third day of incubation significantly increased the rates of apoptosis (p<0.001), irrespective of pre-incubation with TNF-α. These in vitro data suggest that Fas-mediated apoptosis is the common effector pathway of apoptosis in cells expressing TNF superfamily receptors, and attribute a relatively modest role to TNF-α in sensitization of these cells.

Figure 7G:
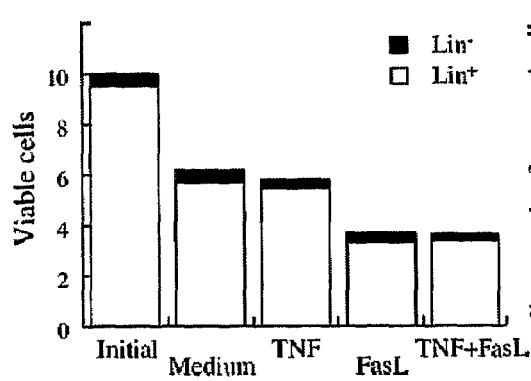
Figure 7H:
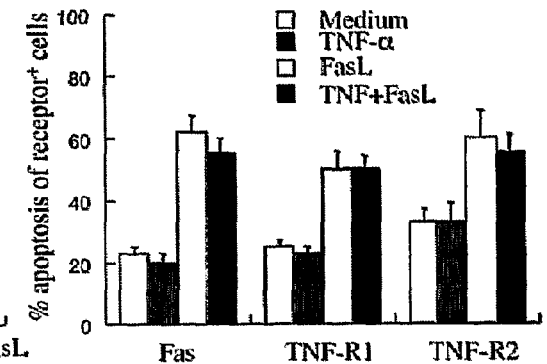
Figure 7I:
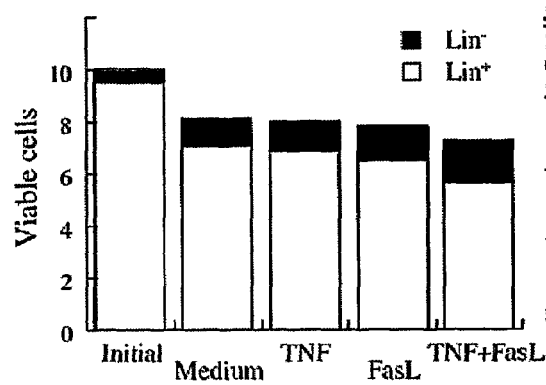
Figure 7J:
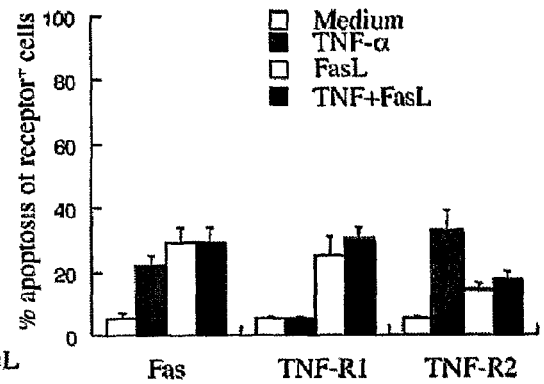
Figure 7K:
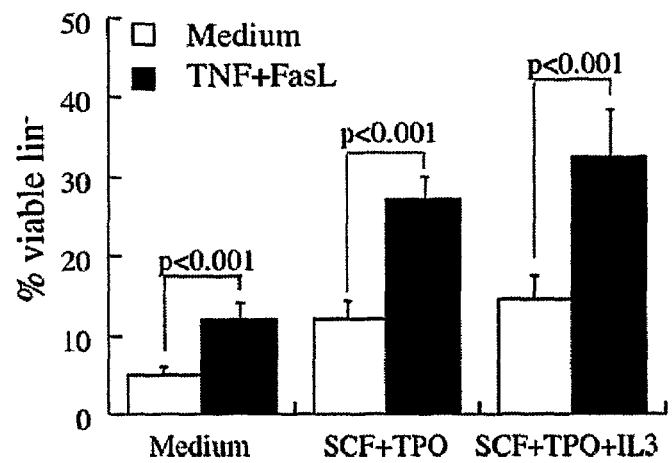

Incubation in the presence of SFC+TPO had a minor effect on the number of cells (FIG. 7G) and the fraction of apoptotic cells (FIG. 7H). However, in the presence of SCF+TPO+IL-3 the number of viable cells increased substantially, in particular the lin$^-$ subset (FIG. 7I). This was accompanied by reduced sensitivity of the receptor-positive cells to apoptosis (FIG. 7J). Further analysis showed that cells expressing the putative stem cell markers Sca-1 and c-kit were largely within the viable fraction of cells. Likewise, during control incubation in supporting medium, 10±2% of the LTR cells and 22±4% of the STR cells stained positive for annexin-V (FIG. 6C). Addition of FasL protein resulted in apoptosis of 40% of the freshly-elutriated STR subset, whereas the LTR subset showed a minor increase in apoptosis. Notably, during this incubation period both LTR and STR cells upregulated their Fas expression to 18±5% and 42±6%, respectively. After 5 days of incubation with TNF and addition of FasL during the last day, there was a 2.3-fold increase in number of viable lin$^-$ BMC, indicating apoptotic death of a significant fraction of the lin$^+$ BMC (FIG. 7K). These data present various approaches for enrichment of the fraction of undifferentiated cells from an initial bone marrow inoculum.

Example 15

The Fas and TNF Receptors Mediate Apoptotic and Non-apoptotic Signals

Figure 8A:
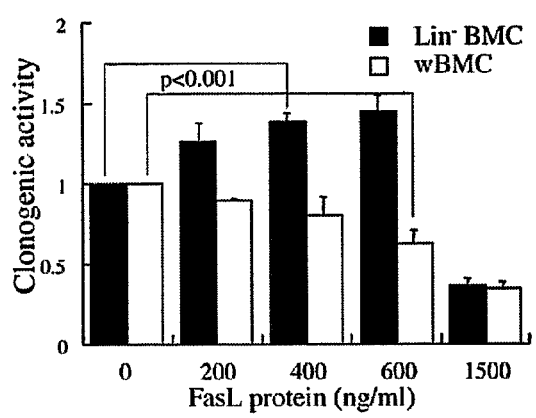
FIGS. 8A-F illustrate the dual trophic and apoptotic functions of death receptors. $3\times10^4$ cells were plated in 1.2% methylcellulose containing 20% fetal bovine serum, 1% bovine serum albumin, 0.1 mM 2$\beta$-Mercaptoethanol, 10 u/ml recombinant human erythropoietin (EPO), 20 ng/ml recombinant mouse (rm) stem cell factor (SCF), 10 ng/ml rm interleukin-3 (IL-3) and 10 ng/ml granulogyte-macrophage colony stimulating factor (rmGM-CSF), in Iscove Modified Dulbecco Medium (IMDM). A. Incubation of whole BMC (wBMC) and lin$^-$ BMC with FasL oligomers in semisolid methylcellulose cultures resulted in a dose dependent increment in the clonogenic activity of lin$^-$ BMC. At high protein concentrations (>1 µg/ml) an abrupt decay in clonogenic activity resembled that observed in whole BMC. The data summarize 8 independent experiments. B. Under same culture conditions, high concentrations (>250 ng/ml) of TNF$\alpha$ stimulated the activity of lin– BMC without affecting the activity of wBMC (n=5). C. The clonogenic activity and death of wBMC and lin$^-$ BMC from Fas-defective (lpr) mice were insensitive to the presence of the FasL protein (n=5). D. Inhibition of caspase-3 with Z-DEVD-fmk and of caspase-8 with Z-IETD-fmk restored the clonogenic activity of whole BMC (n=5). E. Caspase-3 inhibition (DEVD) did not affect the enhanced clonogenicity induced by 500 ng/ml FasL protein in lin$^-$ BMC, and reduced apoptotic death at toxic protein concentrations. F. Inhibition of caspase 3 (DEVD) markedly increased clonogenicity of short-term repopulating cells (STC) isolated by elutriation (n=5).
Figure 8B:
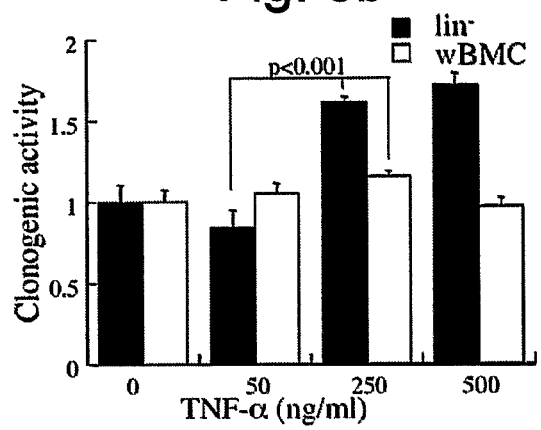

Under physiological conditions, the stem cells and progenitors with hematopoietic reconstituting potential consist of a very small fraction embedded in a bulk mass of progenitors (at various differentiation stages). In distal stages of differentiation the death receptors fill an important role in regulating the size of the expanding clones. These receptors have been identified as negative regulators of terminal differentiation in all hematopoietic lineages (7-14). The acute upregulation of death receptors early after transplantation, in the absence of donor cell sensitivity to apoptosis questioned the role of these receptors. Therefore, the present inventors evaluated modulation of the clonogenic activities of wBMC and lin⁻ BMC by graded increase in FasL and TNF-α under minimal stimulatory conditions. The activity of wBMC was progressively suppressed as the concentration of FasL was increased (FIG. 8A), and was largely unaffected in the presence of TNF-α (FIG. 8B). These data were consistent with the lack of apoptotic signals triggered by TNF-α in naïve BMC (see Example 13). In marked contrast, the clonogenic activity of lin⁻ BMC was gradually stimulated, by 45% and 70% at FasL and TNF-α concentrations of ~500 ng/ml, respectively. This behavior was observed both when soluble FasL oligomers were added to the culture medium, and when the protein was adsorbed to the cell surface via biotinylation (FIG. 8A). FasL became toxic to lin⁻ BMC at a threshold concentration of 1 µg/ml. Consistent with previous reports on lack of significant effect of activating Fas antibodies (Jo2) on colony formation in murine (17) and human HPSC (5,18), a concentration of 5 ng/ml soluble superFasL failed to attenuate the clonogenicity of lin⁻ BMC. Taken together, these data suggest that Fas receptor trimerization is essential for transduction of the growth signals.

The relative clonogenic activities of wBMC and lin⁻ BMC suggests concomitant trophic and apoptotic signaling through the Fas receptor in apoptosis-sensitive and insensitive subsets of cells. In cultures of wBMC, the dead cells might inhibit the clonogenic activity of progenitors. To test this possibility, apoptotic wBMC were added to the culture of lin⁻ BMC in conjunction with 500 ng/ml FasL protein. At a ratio of 1:1 viable lin⁻ BMC to dead BMC, enhanced clonogenesis induced by FasL was abolished, suggesting that viability of the bulk cells impacts colony formation.

Figure 8C:
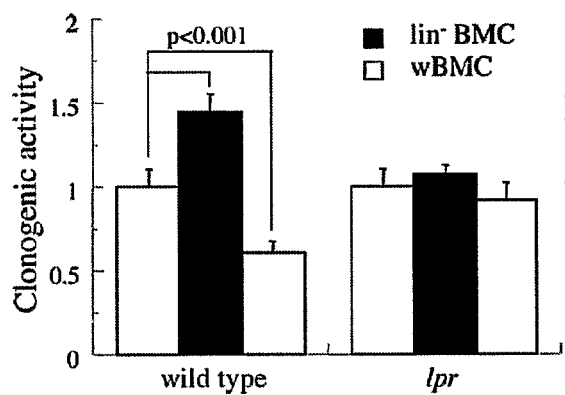

Further assessment was performed at the proximal and distal stages of the apoptotic cascade. To ascertain that FasL affected the cells through binding to the Fas receptor, clonogenic assays were performed with cells harvested from Fas-defective (lpr) mice. The lpr mutation rendered the wBMC and lin⁻ BMC insensitive to the apoptotic and tropic effects of the FasL protein, respectively (FIG. 8C), indicating that modulation of progenitor activity was specifically mediated by Fas receptor ligation. Similar reduced clonogenity was observed upon incubation of the cells with blocking TNF-R1 antibodies, suggesting that this receptor was preferentially involved in trophic signal transduction as compared to TNF-R2.

Figure 8D:
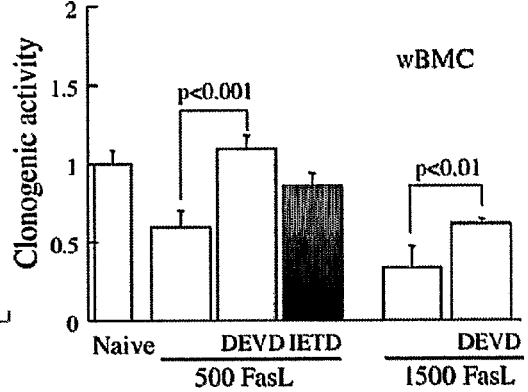
Figure 8E:
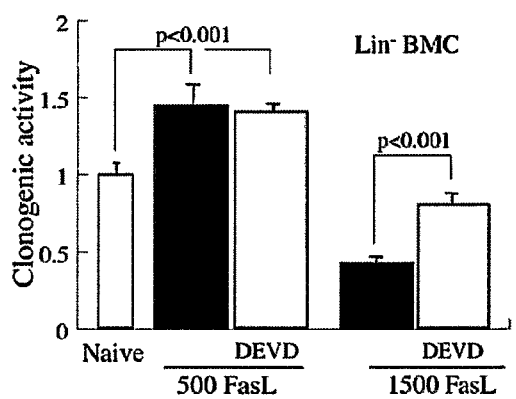

At the distal end of the apoptotic cascade, caspases 3 and 8 were inhibited to minimize apoptotic death in culture. Inhibition of caspases 3 (DEVD) and 8 (IETD) reduced apoptosis and improved the clonogenic activity of wBMC at all FasL concentrations (FIG. 8D). Consistent results were observed upon inhibition of these caspases in clonogenic assays of lin⁻ BMC (FIG. 8E). Addition of the caspase inhibitors in the absence of FasL did not affect significantly clonogenicity. Noteworthy, inhibition of caspase activity did not abrogate the stimulatory effect of 500 ng/ml FasL on lin⁻ BMC, indicating that Fas-mediated tropism was mediated by factors proximal to caspase-8 activation.

Figure 8F:
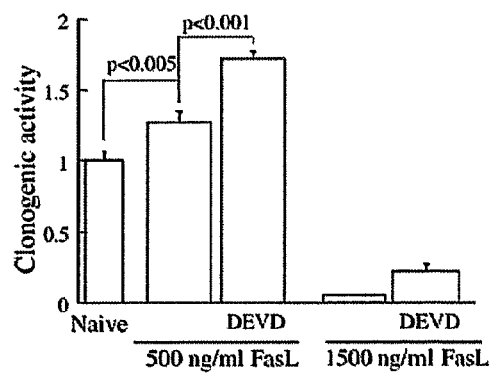

Analysis of elutriated cell populations showed null clonogenic activity of LTR cells (5 colonies in one culture and four null cultures) independent of the presence of FasL, as anticipated and previously reported for these cells [34,35]. In marked variance, the clonogenic activity of STR cells was increased by 26±6% ($p<0.005$) in the presence of a supralethal concentration of 500 ng/ml FasL protein (FIG. 8F). A FasL concentration of 1.5 µg/g completely abolished the clonogenic activity of these progenitors. To evaluate the equilibrium between trophic and apoptotic signals mediated by the Fas receptor, inhibition of common effector caspase-3 (DEVD) further enhanced the pro-clonogenic effect of FasL to 75±5% ($p<0.001$ vs naïve and cultures without caspase-3 inhibition). Taken together, these data indicate that the subset of early hematopoietic reconstituting cells (STR) receive dual apoptotic and trophic signals through the Fas receptor.

Example 16

Resistance of Progenitors to Apoptosis During Stress Hematopoiesis

Results

Insensitivity of naïve or transplanted bone marrow-derived HSPC to apoptotic signals questioned whether the mechanisms mediated by death receptors also operate under conditions of stress hematopoiesis. 5-fluorouracil (5FU) is toxic to fast cycling progenitors, and their killing induces synchronized stimulation of the primitive hematopoietic progenitors in the bone marrow. To activate and synchronize the hematopoietic progenitors, mice were injected with 150 µg/g 5-fluorouracil (5FU) and their bone marrow cells were harvested 1, 3 and 5 days later. After 5 days, the incidence of Sca-1 expression increased to 29±2% ($p<0.001$ vs 2±1% in naïve BMC), the incidence of c-kit expression increased to 12±2% ($p<0.05$ vs 8±1.5% in naïve BMC) and the fraction of Sca-1$^+$c-kit$^+$ increased to 5±0.9% ($p<0.001$ vs 0.4±0.1 in naïve BMC) (FIG. 9A). These changes were accompanied by up-regulation of the Fas receptor and its ligand ($p<0.001$) (FIG. 9B), including the fraction of lin⁻ BMC that expressed low levels of these molecules under steady state conditions (FIG. 9C). Similar changes, at lower magnitudes were observed for the TNF and TRAIL receptors. Cells harvested at this time were challenged with the FasL protein for an additional period of 18 hours of ex vivo incubation. Both lin⁻ and lin⁺ subsets showed remarkable superior viability after incubation with FasL protein as compared to BMC harvested from naïve mice (FIG. 9D). To display the relationship between Fas expression and apoptosis, the receptor was quantified by flow cytometry after ex vivo incubation of cells harvested 1, 3, and 5 days after 5FU injection. Display of the fractional cell death as a function of Fas expression showed several features (FIG. 9E-F). First, the expression of Fas increased with time after 5FU administration. Second, exposure of the cells to FasL ex vivo (FIG. 9F) further enhanced the expression of the receptor as compared to cells incubated in medium (FIG. 9E). Third, most Fas⁺ BMC were insensitive to FasL-induced apoptosis after 5FU treatment. Taken together, these data indicated that developing progenitors were more susceptible to FasL-induced up-regulation of the Fas receptor, without concomitant sensitization to apoptosis. These data indicate that death receptors, in particular Fas, play a trophic role in the physiological function of the hematopoietic system under stress conditions.

Discussion

Unlike most somatic cells, stem cells are often required to perform differentiation tasks under extreme conditions of injury and inflammation. The requirement of the pluripotent capacity of adult stem cells to participate in tissue repair, in particular to differentiate and adopt functional characteristics of the injured tissue, imposes questions on the ability of these cells to survive and operate within a hostile environment. A well-established procedure is hematopoietic stem and progenitor cell (HSPC) transplantation, which often follows aggressive chemotherapy and radiation that inflict severe injury to the bone marrow. Endogenous hematopoietic cells rarely survive myeloablative radiation, and the stroma is severely damaged. In the aftermath of ablative injury, donor HSPC find their way to the host bone marrow where they seed and engraft to reconstitute the immune-hematopoietic system. In this process, acute up-regulation of the death receptors was found in a significant fraction of donor cells. Prior work has attributed to the death receptors a detrimental role in hematopoietic cell function, concepts adopted from the inhibitory function of the receptors in the distal stages of differentiation in the immune-hematopoietic system. In contrast, the present inventors found a positive role of the death receptors in stem cell function. The mechanisms by which hematopoietic reconstituting cells flourish in such a devastated environment is of particular interest, as it may be used to improve the efficiency of engraftment.

In summary, the present inventors have shown:

1. Death receptors are expressed at low levels in bone marrow cells under steady state conditions. The receptors are acutely up-regulated under conditions of stimulated hematopoiesis, including transplantation.

2. The most primitive subsets of stem and progenitor cells express all death receptors.

3. In progenitors with hematopoietic reconstituting potential the death receptors do not mediate apoptotic signals.

4. The same receptors that mediate death in distal stages of differentiation and in somatic cells mediate trophic signals in most primitive hematopoietic stem and progenitor cells.

5. Elimination of non-stem cells using death signals does not affect the short-term hematopoietic reconstituting potential of progenitors and the long-term reconstitution potential of stem cells.

6. Death receptor expression at the transcriptional level is induced by multiple intrinsic and extrinsic factors. These include the release of factors in response to injury, interaction with stroma, cycling and differentiation.

7. Constitutive and enforced expression of Fas-ligand augments hematopoietic cell engraftment through abrogation of alloimmune responses and non-immunogenic mechanisms.

8. Induced expression and activation of the death receptors ex vivo is efficient in depletion of non-stem cells through apoptotic signals.

Taken together, these data point to a distinct mode of action of death receptors of the TNF superfamily in stem and progenitor cells. Under physiological conditions, signals that induce HSPC activation also induce expression of death receptors. This was exemplified by 5FU-synchronized activation of progenitor activity, which was accompanied by progressive expression of the Fas receptor. However the pool of activated progenitors was largely insensitive to Fas-mediated apoptosis: a 3-4 fold increase in the fraction of Fas$^+$ cells was associated with resistance to FasL-induced apoptosis of the vast majority of the cells after 5 days. These data suggest that Fas is up regulated early after 5FU administration, possibly due to skewed cytokine environment caused by intrabone marrow cell death, and acts to promote the growth of hematopoietic progenitors. The Fas receptor resumes its function as a negative regulator of the pool of developing progenitors only in the distal stages of the differentiation traits (7-14).

In the transplant setting, the following scenario is proposed for the involvement of the Fas/FasL signaling pathway in the early stages of hematopoietic cell engraftment. Upon donor cell homing to the bone marrow, the inflammatory environment and interaction with the stroma induces expression of the receptor and ligand. The expression of Fas converts the donor cells responsive to environmental factors that modulate their activity, influences that are rather supportive than detrimental to hematopoietic cell engraftment. Elimination of the more differentiated progenitors by apoptosis increases the engraftment chances of more primitive stem and progenitor cells. This may be considered as a mechanism of HSPC enrichment within the process of seeding and early engraftment, in continuation of an earlier enrichment process attributed to superior homing of HSPC as compared to committed progenitors (1). Resistance to Fas-mediated apoptotic death evolves as a functional characteristic of those donor cells that engraft successfully. This characteristic endows the primitive progenitors with the ability to counterattack immune reactions using ligands of the TNF superfamily (32-34).

Expression of the TNF-superfamily death receptors may be a physiological response of immune-hematopoietic cells upon encountering a hostile environment, or exposure to stress conditions. Stem and progenitor cells endowed with these protective factors guarantee the maintenance of the important element in this developmental system. In apoptosis-resistant progenitors, these receptors are associated with trophic signaling that aid in recruiting the primitive precursors to differentiate and proliferate. This mechanism not only protects the most important element in this developmental system, the stem cells, but also participates in their activation under extreme conditions of injury. Previous studies have demonstrated that hematopoietic progenitors are protected from apoptosis by high levels of anti-apoptotic factors, including FLIP, Bcl-2, survivin and the unique expression of caspase-8L (5,6). The present data indicate that trophic signaling deviates from the major pathway of death-receptor-associated apoptotic signaling proximal to caspase-8 activation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

REFERENCES

1. Yaniv I, Stein J, Farkas D L, Askenasy N. The tale of early hematopoietic cell seeding in the bone marrow niche. Stem Cells & Development. 2006; 15:4-16.

2. Ashkenazi A. Targeting death and decoy receptors of the tumour-necrosis factor superfamily. Nat Cancer Rev. 2002; 2:420-430.

3. Askenasy N, Yolcu E S, Yaniv I, Shirwan H. Induction of tolerance using Fas ligand: a double-edged immunomodulator. Blood. 2005; 105:1396-1404.

4. Niho Y, Asano Y. Fas/Fas ligand and hematopoietic progenitor cells. Curr Opin Hematol. 1998; 5:163-165.

5. Kim H, Whartenby K A, Georgantas R W 3rd, Wingard J, Civin C I. Human CD34+ hematopoietic stem/progenitor cells express high levels of FLIP and are resistant to Fas-mediated apoptosis. Stem Cells. 2002; 20: 174-182.

6. Mohr A, Zwacka R M, Jarmy G, Buneker C, Schrezenmeier H, Dohner K, Beltinger C, Wiesneth M, Debatin K M, Stahnke K. Caspase-8L expression protects CD34+ hematopoietic progenitor cells and leukemic cells from CD95-mediated apoptosis. Oncogene. 2005; 24:2421-2429.

7. Bhardwaj A, Aggarwal B B. Receptor-mediated choreography of life and death. J Clin Immunol. 2003; 23:317-332.

8. Dempsey P W, Doyle S E, He J Q, Cheng G. The signalling adaptors and pathways activated by TNF superfamily. Cytokine Growth Factor Rev. 2003; 14:193-209.

9. Greil R, Anether G, Johrer K, Tinhofer I. Tuning the rheostat of the myelopoietic system via Fas and TRAIL. Crit Rev Immunol. 2003; 23:301-322.

10. Gaur U, Aggarwal B B. Regulation of proliferation, survival and apoptosis by members of the TNF superfamily. Biochem Pharmacol. 2003; 66:1403-1408.

11. Ware C F. The TNF superfamily. Cytokine Growth Factor Rev. 2003; 14:181-184.

12. Di Pietro R, Zauli G. Emerging non-apoptotic functions of tumor necrosis factor-related apoptosis-inducing ligand (TRAIL)/Apo2L. J Cell Physiol. 2004; 201:331-340.

13. Testa U. Apoptotic mechanisms in the control of erythropoiesis. Leukemia. 2004; 18:1176-1199.

14. Zauli G, Secchiero P. The role of the TRAIL/TRAIL receptors system in hematopoiesis and endothelial cell biology. Cytokine Growth Factor Rev. 2006; 17:245-257.

15. Takenaka K, Nagafuji K, Harada M, Mizuno S, Miyamoto T, Makino S, Gondo H, Okamura T, Niho Y. In vitro expansion of hematopoietic progenitor cells induces functional expression of Fas antigen (CD95). Blood. 1996; 88:2871-2877.

16. Stahnke K, Hecker S, Kohne E, Debatin KM. CD95 (APO-1/FAS)-mediated apoptosis in cytokine-activated hematopoietic cells. Exp Hematol. 1998; 26:844-850.

17. Bryder D, Ramsfjell V, Dybedal I, Theligaard-Monch K, Hogerkorp C M, Adolfsson J, Borge O J, Jacobsen S E. Self-renewal of multipotent long-term repopulating hematopoietic stem cells is negatively regulated by Fas and tumor necrosis factor receptor activation. J Exp Med 2001; 194: 941-952.

18. Dybedal I, Yang L, Bryder D, Aastrand-Grundstrom I, Leandersson K, Jacobsen S E. Human reconstituting hematopoietic stem cells up-regulate Fas expression upon active cell cycling but remain resistant to Fas-induced suppression. Blood. 2003; 102:118-126.

19. Maciejewski J, Selleri C, Anderson S, Young N S. Fas antigen expression on CD34+ human marrow cells is induced by interferon gamma and tumor necrosis factor alpha and potentiates cytokine-mediated hematopoietic suppression in vitro. Blood. 1995; 85:3183-3190.

20. Sato T, Selleri C, Anderson S, Young N S, Maciejewski J P. Expression and modulation of cellular receptors for interferon-gamma, tumour necrosis factor, and Fas on human bone marrow CD34+ cells. Br J Haematol. 1997; 97:356-365.

21. 1998; 26:1202-1208.

22. Yang L, Dybedal I, Bryder D, Nilsson L, Sitnicka E, Sasaki Y, Jacobsen SE. IFN-gamma negatively modulates self-renewal of repopulating human hemopoietic stem cells. J Immunol. 2005; 174:752-757.

23. Moore M A S. Cytokine and chemokine networks influencing stem cell proliferation, differentiation and marrow homing. J Cell Biochem. 2002; 38:29-38.

24. Aggarwal B B. Signalling pathways of the TNF superfamily: a double-edged sword. Nat Rev Immunol. 2003; 3:745-756.

25. Curtin J F, Cotter T G. Live and let die: regulatory mechanisms in Fas-mediated apoptosis. Cell Signal. 2003; 15:983-992.

26. Wajant H, Pfizeiimaier K, Scheurich P. Non-apoptotic Fas signaling. Cytokine Growth Factor Rev. 2003; 14:53-66.

27. Park S M, Schickel R, Peter M E. Nonapoptotic functions of FADD-binding death receptors and their signaling molecules. Curr Opin Cell Biol. 2005; 17:610-6

28. Liu B, Buckley S M, Lewis I D, Goldman A I, Wagner J E, van der Loo J C. Homing defect of cultured human hematopoietic cells in the NOD/SCID mouse is mediated by Fas/CD95. Exp Hematol. 2003; 31:824-832.

29. Barcena A, Muench M, Song K S, Ohkubo T, Harrison M R. Role of CD95/Fas and its ligand in the regulation of the growth of human CD34$^{++}$ CD38$^{-}$ fetal liver cells. Exp Hematol. 1999,27:1428-14339.

30. Josefsen D, Myklebust J H, Lynch D H, Stokke T, Blomhoff H K, Smeland E B. Fas ligand promotes cell survival of immature human bone marrow CD34+CD38− hematopoietic progenitor cells by suppressing apoptosis. Exp Hematol. 1999; 27:1451-1459.

31. Saheki K, Fujimori Y, Takemoto Y, Kakishita E. Increased expression of Fas (APO-1, CD95) on CD34+ haematopoietic progenitor cells after allogeneic bone marrow transplantation. Br J Haematol. 2000; 109:447-452.

32. Gur H, Krauthgamer R, Bachar-Lustig E, Katchman H, Arbel-Goren R, Berrebi A, Klein T, Nagler A, Tabilio A, Martelli M F, Reisner Y. Immune regulatory activity of CD34+ progenitor cells: evidence for a deletion-based mechanism mediated by TNF-alpha. Blood. 2005; 105:2585-2593.

33. Whartenby K A, Straley E E, Kim H, Racke F, Tanavde V, Gorski K S, Cheng L, Pardoll D M, Civin C I. Transduction of donor hematopoietic stem-progenitor cells with Fas ligand enhanced short-term engraftment in a murine model of allogeneic bone marrow transplantation. Blood. 2002; 100:3147-3154.

34. Pearl-Yafe M, Yolcu E S, Stein J, Kaplan O, Yaniv I, Shirwan H, Askenasy N. Fas-ligand enhances hematopoietic cell engraftment through abrogation of alloimmune responses and non-immunogenic interactions. Stem Cells. 2007; in press 35. Bohana-Kashtan O, Civin C I. Fas ligand as a tool for immunosuppression and generation of immune tolerance. Stem Cells. 2004; 22:908-924.

36. Pearl-Yafe M, Yolcu E S, Yaniv I, Stein J, Shirwan H, Askenasy N. The dual role of Fas-ligand as an injury effector and defense strategy in diabetes and islet transplantation. Bioessays. 2006; 28:211-222.

What is claimed is:

1. A method of selecting stem cells from a heterogeneous population of mammalian cells containing stem cells and non-stem cells, the method comprising contacting the population of cells with a polypeptide agent selected from the group consisting of TNF-α, FasL, Trail and Tweak, wherein said contacting induces apoptosis of non-stem cells while stem cells remain resistant to the apoptotic signal, thereby selecting the stem cells from the heterogeneous population of cells.

2. The method of claim 1, wherein said stem cells are selected from the group consisting of umbilical cord blood stem cells, mobilized peripheral blood stem cells, bone marrow stem cells and neural stem cells.

3. The method of claim 2, wherein said stem cells are bone marrow stem cells.

4. The method of claim 3, wherein said bone marrow stem cells are hematopoietic stem cells.

5. The method of claim 1, further comprising modifying said stem cells prior to the contacting so as to generate modified stem cells.

6. The method of claim 1, further comprising purifying said stem cells prior to the contacting so as to generate purified stem cells.

7. The method of claim 1, further comprising expanding said stem cells prior to the contacting so as to generate expanded stem cells.

8. The method of claim 3, wherein said bone marrow stem cells are mesenchymal stem cells.

9. The method of claim 1, wherein said stem cells are adult stem cells.

10. The method of claim 1, wherein said stem cells are embryonic stem cells.

11. The method of claim 1, wherein said apoptosis inducing agent is FasL.

12. The method of claim 11, wherein said FasL is conjugated to a surface.

13. The method of claim 12, wherein said FasL is non-cleavable.

14. The method of claim 1, further comprising inducing up-regulation of expression of an apoptosis receptor on said heterogeneous population of cells prior to said contacting, said apoptosis receptor being selected from the group of receptors consisting of a Fas receptor, a TNF-α receptor, a Tweak receptor and a Trail receptor.

15. The method of claim 14, wherein said inducing up-regulation of expression of said apoptosis receptor is effected by contacting said heterogeneous population of cells with Interferon γ or TNF-α.

16. The method of claim 1, wherein said heterogeneous population of cells does not comprise activated T lymphocytes.

17. The method of claim 1, wherein the heterogeneous population of cells comprises apoptosis sensitive lineage positive cells.

18. The method of claim 17, wherein said apoptosis sensitive lineage positive cells are selected from the group consisting of granulocytes, macrophages, natural killer cells, erythroblasts, antigen presenting cells, myeloid cells, lymphoid cells, and megakaryocytes.

19. The method of claim 1, wherein the heterogeneous population of cells comprises apoptosis sensitive malignant cells.

20. The method of claim 1, further comprising isolating the stem cells following said contacting.

21. A method of transplanting selected stem cells into a host, the method comprising:
(a) contacting stem cells of a heterogeneous population of mammalian cells comprising both stem cells and non-stem cells with a polypeptide agent selected from the group consisting of TNF-α, FasL, Trail and Tweak, wherein said contacting induces apoptosis of non-stem cells, while stem cells remain resistant to the apoptotic signal, to thereby select stem cells; and
(b) transplanting said selected stem cells into a host, thereby transplanting said selected stem cells.

22. The method of claim 21, further comprising isolating said selected stem cells following step (a) and prior to step (b).

23. The method of claim 21, wherein said stem cells are selected from the group consisting of umbilical cord blood stem cells, mobilized peripheral blood stem cells, bone marrow stem cells and neural stem cells.

24. The method of claim 23, wherein said stem cells are bone marrow stem cells.

25. The method of claim 24, wherein said bone marrow stem cells are hematopoietic stem cells.

26. The method of claim 21, further comprising modifying said stem cells prior to the contacting so as to generate modified stem cells.

27. The method of claim 21, further comprising purifying said stem cells prior to the contacting so as to generate purified stem cells.

28. The method of claim 21, further comprising expanding said stem cells prior to or during the contacting so as to generate expanded stem cells.

29. The method of claim 24, wherein said bone marrow stem cells are mesenchymal stem cells.

30. The method of claim 21, wherein said stem cells are adult stem cells.

31. The method of claim 21, wherein said stem cells are embryonic stem cells.

32. The method of claim 21, wherein said apoptosis inducing agent is FasL.

33. The method of claim 32, wherein said FasL is conjugated to a surface.

34. The method of claim 33, wherein said FasL is non-cleavable.

35. The method of claim 21, further comprising inducing up-regulation of expression of an apoptosis receptor on said heterogeneous population of cells prior to said contacting, wherein said apoptosis receptor is selected from the group consisting of a Fas receptor, a TNF-α receptor, a Tweak receptor and a Trail receptor.

36. The method of claim 35, wherein said inducing up-regulation of expression of said apoptosis receptor is effected by contacting said heterogeneous population of cells with Interferon γ or TNF-α.

37. The method of claim 21, wherein said heterogeneous population of cells does not comprise activated T lymphocytes.

38. The method of claim 21, wherein the heterogeneous population of cells comprises apoptosis-sensitive lineage positive cells.

39. The method of claim 38, wherein said apoptosis-sensitive lineage positive cells are selected from the group consisting of granulocytes, macrophages, natural killer cells, erythroblasts, antigen presenting cells, myeloid cells, lymphoid cells, erythroid cells and megakaryocytic cells.

40. The method of claim 21, wherein the heterogeneous population of cells comprises apoptosis-sensitive malignant cells.

41. The method of claim 21, wherein said stem cells are autologous to the host.

42. The method of claim 21, wherein said stem cells are syngeneic to the host.

43. The method of claim 21, wherein said stem cells are allogeneic to the host.

44. The method of claim 21, wherein said stem cells are xenogeneic to the host.

45. A method of differentiating stem cells, the method comprising:
(a) contacting stem cells of a heterogeneous population of mammalian cells comprising both stem cells and non-stem cells with a polypeptide agent selected from the group consisting of TNF-α, Fast, Trail, and Tweak, wherein said contacting induces apoptosis of non-stem cells while stem cells remain resistant to the apoptotic signal, to thereby select stem cells; and
(b) inducing differentiation of said selected stem cells, thereby differentiating stem cells.

46. The method of claim 45, wherein said inducing differentiation is effected by expressing a gene product in said stem cells.

47. The method of claim 46, wherein said gene product is a polypeptide.

48. The method of claim 46, wherein said gene product is a polynucleotide.

* * * * *

UNITED STATES PATENT AND TRADEMARK OFFICE
CERTIFICATE OF CORRECTION

PATENT NO.         : 8,435,786 B2
APPLICATION NO.    : 12/227865
DATED              : May 7, 2013
INVENTOR(S)        : Nadir Askenasy Page 1 of 1

It is certified that error appears in the above-identified patent and that said Letters Patent is hereby corrected as shown below:

In the Claims

Claim 45, column 42, line 34, delete "Fast" and insert --FasL--.

Signed and Sealed this
Third Day of December, 2013

Margaret A. Focarino
*Commissioner for Patents of the United States Patent and Trademark Office*

SEQUENCE LISTING

<160> NUMBER OF SEQ ID NOS: 4

<210> SEQ ID NO 1
<211> LENGTH: 17
<212> TYPE: DNA
<213> ORGANISM: Artificial sequence
<220> FEATURE:
<223> OTHER INFORMATION: Single strand DNA oligonucleotide

```
<400> SEQUENCE: 1
gccttggttg ttgacca                                                    17

<210> SEQ ID NO 2
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 2
gtaccagcac aggagca                                                    17

<210> SEQ ID NO 3
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 3
accgccatca caacca                                                     16

<210> SEQ ID NO 4
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 4
tcaacctctt ctcctcca                                                   18
```